US008734813B2

(12) United States Patent
Ryall

(10) Patent No.: US 8,734,813 B2
(45) Date of Patent: *May 27, 2014

(54) MULTIVALENT MENINGOCOCCAL POLYSACCHARIDE-PROTEIN CONJUGATE VACCINE

(71) Applicant: Sanofi Pasteur Inc., Swiftwater, PA (US)

(72) Inventor: Robert P. Ryall, East Stroudsburg, PA (US)

(73) Assignee: Sanofi Pasteur, Inc., Swiftwater, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/843,037

(22) Filed: Mar. 15, 2013

(65) Prior Publication Data

US 2013/0216571 A1 Aug. 22, 2013

Related U.S. Application Data

(60) Continuation of application No. 13/738,698, filed on Jan. 10, 2013, which is a division of application No. 10/054,638, filed on Jan. 22, 2002.

(60) Provisional application No. 60/263,435, filed on Jan. 23, 2001.

(51) Int. Cl.
*A61K 39/095* (2006.01)
*A61K 39/385* (2006.01)
*A61K 39/02* (2006.01)
*A61K 39/00* (2006.01)
*A01N 43/04* (2006.01)
*C07H 1/00* (2006.01)

(52) U.S. Cl.
USPC ........... 424/250.1; 424/203.1; 424/234.1; 424/190.1; 424/184.1; 514/23; 536/123

(58) Field of Classification Search
None
See application file for complete search history.

(56) References Cited

U.S. PATENT DOCUMENTS

| 4,351,761 A | 9/1982 | Gaafar |
|---|---|---|
| 4,356,170 A | 10/1982 | Jennings |
| 4,619,828 A | 10/1986 | Gordon |
| 4,761,283 A | 8/1988 | Anderson |
| 4,762,713 A | 8/1988 | Anderson |
| 4,814,276 A | 3/1989 | Evans |
| 4,963,534 A | 10/1990 | Calabria |
| 5,153,312 A | 10/1992 | Porro |
| 5,314,811 A | 5/1994 | Lee |
| 5,422,427 A | 6/1995 | Russell |
| 5,445,817 A | 8/1995 | Schneerson |
| 5,811,102 A | 9/1998 | Jennings et al. |
| 5,965,714 A | 10/1999 | Ryall |
| 6,007,818 A | 12/1999 | Moreau |
| 6,013,264 A | 1/2000 | Petre et al. |
| 6,045,805 A | 4/2000 | Moreau |
| 6,087,328 A | 7/2000 | Lees |
| 6,146,902 A | 11/2000 | McMaster |
| 6,248,334 B1 | 6/2001 | Lees et al. |
| 6,248,570 B1 | 6/2001 | Michon |
| 6,413,520 B1 | 7/2002 | Granoff |
| 6,632,437 B1 | 10/2003 | Schneerson |
| 2002/0054879 A1 | 5/2002 | Lees |
| 2002/0054884 A1 | 5/2002 | Peetermans |
| 2002/0182226 A1 | 12/2002 | Peetermans |
| 2003/0068336 A1 | 4/2003 | Ryall |
| 2003/0157129 A1 | 8/2003 | Siaoui |
| 2005/0106181 A1 | 5/2005 | Constantino |
| 2005/0208605 A1 | 9/2005 | Stanton et al. |
| 2009/0130147 A1 | 5/2009 | Constantino |

FOREIGN PATENT DOCUMENTS

| EP | 833662 | 11/1987 |
|---|---|---|
| EP | 398615 | 7/1993 |
| EP | 245045 | 11/1993 |
| EP | 831901 | 4/1998 |
| EP | 833662 | 4/1998 |
| EP | 528635 | 2/1999 |
| EP | 630260 | 1/2001 |
| EP | 831901 B1 | 9/2001 |
| EP | 562107 | 5/2002 |
| EP | 1835939 | 9/2007 |
| WO | 8706838 | 11/1987 |
| WO | 9006696 | 6/1990 |
| WO | 9216232 | 10/1992 |
| WO | 9307178 | 4/1993 |
| WO | 9640242 | 12/1996 |
| WO | 9700697 | 1/1997 |
| WO | 9830239 | 7/1998 |

(Continued)

OTHER PUBLICATIONS

Cessey, et al., The Journal of Infectious Diseases, 167:1212-1216 (1993).

(Continued)

*Primary Examiner* — S. Devi

(74) *Attorney, Agent, or Firm* — Pierce Atwood, LLP; Raymond G. Arner

(57) ABSTRACT

The present invention describes a combined vaccine that offers broad protection against meningococcal disease caused by the pathogenic bacteria *Neisseria meningitidis*. The vaccine is comprised of four distinct polysaccharide-protein conjugates that are formulated as a single dose of vaccine. Purified capsular polysaccharides from *Neisseria meningitidis* serogroups A, C, W-135, and Y are chemically activated and selectively attached to a carrier protein by means of a covalent chemical bond, forming polysaccharide-protein conjugates capable of eliciting long-lasting immunity to a variety of *N. meningitidis* strains in children as well as adults.

64 Claims, No Drawings

(56) References Cited

FOREIGN PATENT DOCUMENTS

| WO | 9832873 | 10/1998 |
|---|---|---|
| WO | 9845312 | 10/1998 |
| WO | 9847530 | 10/1998 |
| WO | 9854296 | 12/1998 |
| WO | 9858670 | 12/1998 |
| WO | 9918121 | 4/1999 |
| WO | 9932653 | 7/1999 |
| WO | 9942130 | 8/1999 |
| WO | 0038711 | 7/2000 |
| WO | 0056360 | 9/2000 |
| WO | 0071725 | 11/2000 |
| WO | 0109350 | 2/2001 |
| WO | 0130390 | 5/2001 |
| WO | 0141800 | 6/2001 |
| WO | 0200249 | 1/2002 |

OTHER PUBLICATIONS

Wyle, et al, The Journal of infectious Diseases, 126:514-522 (1972).
Jennings, et al., The Journal of Immunology, 127:1011-1018 (1981).
Anderson, et al., The Journal of Immunology, 137:1181-1186 (1986).
Bartlet, Journal of Biological Chemistry, 234:466-468 (1959).
Svennerholm, et al., Biochimica Biophysica Acta, 24:604-611 (1955).
Park, et al., Journal of Biological Chemistry, 181:149-151 (1949).
Snyder, et al., Analytical Biochemistry, 64:282-288 (1975).
Lowry, et al., Journal of Biological Chemistry 193:265-275 (1951).
Declaration of Dennis I. Kasper, M.D. in Support of Constantino Substantive Motion 5 (Interference 105,830).
Declaration of Dennis I. Kasper, M.D. in Support of Constantino Substantive Motion 8 (Interference 105,830).
Declaration of Neil Ravenscroft, Ph.D. in Support of Constantino Substantive Motion 5 (Interference 105,830).
Declaration of James A. Fiorato. in Support of Constantino Substantive Motion 7 (Interference 105,830).
Declaration of Neil Ravenscroft, Ph.D. in Support of Constantino Substantive Motion 7 (Interference 105,830).
Kasper Declaration in Support of Constantino Opposition to Ryall Combined Motions 1 and 2 (Interference 105,830).
Robert Jones, Waybach Machine, Internet Forensics (O'Reilly 2006):80-82.
Transcript of the Cross-Examination of William Dick, Ph.D., May 18, 2012 (Interference 105,830).
Transcript of the Cross-Examination of Evan H. Dygert, May 18, 2012 (Interference 105,830).
Declaration of Dr. Stephen I. Pelton, M.D. (Interference 105,830).
Declaration of William Dick, Ph.D. (Interference 105,830).
Second Declaration of Stephen I. Pelton, M.D. (Interference 105,830).
Declaration of Mr. Evan H. Dygert (Interference 105,830).
http://support.microsoft.com/kb/299648.
Path to Ryall slides.
www.fda.gov file system modified dates of webpages and files.
Deposition Transcript for William Dick (Interference 105,830).
Deposition Transcript for Evan H. Dygert (Interference 105,830).
Declaration of Robert P. Ryall (Interference 105,830).
Second Declaration of Evan H. Dygert (Interference 105,830).
Attorney general FOIA Guidelines, Sep. 3, 1999.
Ryall Abstract.
Declaration of Angie Bricco (Interference 105,830).
Cadoz, et al., Vaccine 3:340-342 (1985).
Beuvery, et al., Infect. Immun. 41:609-617 (1983).
Fusco, et al., Expert Opin. Investig. Drugs, 7:245-252 (1998).
Lingappa, et al., Vaccine 19:4566-4575 (2001).
Perkins, Jama 283:2842-2843 (2000).
Morley, et al., Vaccine 20:666-687 (2001).
Tai, et al., In: Abstracts of the Tenth International Pathogenic Neisseria Conference (Ed) Zollinger, et al. 214-215 (1996).
Avandano, et al., Pediatric Infect. Dis. J., 12:638-643 (1993).
Ambrosch, et al, Bull. WHO 61:317-323 (1983).
Andre, et al., In: Modern Vaccinology (Ed) Kurstak, et al., Penum medical Book Company, 41-54 (1994).
Levine, et al., In: Abstracts of the Tenth International Pathogenic Neisseria Conference (Ed) Zollinger, et al., 228-230 (1997).
Constantino, et al., Vaccine 10:691-698 (1992).
Lieberman, et al., JAMA 275:1499-1503 (1996).
Twumasi, et al., J. Infect. Dis., 171:632-638 (1995).
Lindberg, Vaccines 17:S28-S36 (1999).
Giebink, et al., The Journal of Infectious diseases, 167:347-355 (1993).
Campagne, et al., Pediatric infectious Disease Journal, 19:144-150 (2000).
Paoletti, et al., Infection and Immunity, vol. 62:3236-3243 (1994).
Bundel, et al., The Journal of Biological Chemistry, vol. 249:2275-2281 (1974).
Gotschlich, et al., J. Exp Med, vol. 129:1349-1365 (1969).
Jennings, et al., The Journal of Infectious diseases, 136: S78-S83 (1977).
Goebel, et al., J. Exp Med, 68:469-481 (1938).
Kayhty, et al., The Journal of Infectious Diseases, 142:861-868 (1980).
Robbins, Immunochemistry, 15:839-854 (1978).
Lamb, David, H., et al., Poster Panels, International Association for Biologicals (IABs), Marcel Merieux Foundation . . . Symposium, Les Pensieres, Veyrier-du-Lac, France (Nov. 30, 1999-Dec. 1, 1999) "Capillary Electrophoretic Analysis of Meningococcal Polysaccharide-Protein Conjugate Vaccines".
Lamb, David, H., et al., Abstract, International Association for Biologicals (IABs), Marcel Merieux Foundation . . . Symposium, Les Pensieres, Veyrier-du-Lac, France (Nov. 30, 1999-Dec. 1, 1999) "Capillary Electrophoretic Analysis of Meningococcal Polysaccharide-Protein Conjugate Vaccines".
Lei, Q., .P., et al., Publication Submission, International Association for Biologicals (IABs), Marcel Merieux Foundation Symposium, Les Pensieres, Veyrier-du-Lac, France (Nov. 30, 1999-Dec. 1, 1999) "Quantitation of Unconjugated Polysaccharide in Diphtheria Toxoid-Conjugate Meningococcal Vaccine by HPAEC/PAD Following Rapid Separation by DOC/HCL".
Lei, Q., P., et al., Abstract, International Association for Biologicals (IABs), Marcel Merieux Foundation . . . Symposium, Les Pensieres, Veyrier-du-Lac, France (Nov. 30, 1999-Dec. 1, 1999) "Quantitation of Unconjugated Polysaccharide in Diphtheria Toxoid-Conjugate Meningococcal Vaccine by HPAEC/PAD Following Rapid Separation by DOC/HCL".
Advisory Committe on Immunization Practices, CDC, Atlanta, GA, Oct. 18-19, 2000, pp., 1-9, 42-44.
Anderson, Edwin, L, et al., Infection and Immunity, 62:3391-3395 (1994).
Campagne, G., et al., Amer. Soc. Tropical Med. & Hygiene, 46th Annual Meeting, Abstract No. 81, Dec. 7-11, 1997.
Fusco, Peter, C., et al., Expert Opinion on Investigational Drugs, 7:245-252 (1998).
Fusco, Peter, C., et al., Intersci. Conf. Agents Chemother., Abstract No. 251, 39:362, Sep. 26-29, 1999.
Global Alliance for Vaccines and Immunization, 4th Board Meeting, Noordwijk.
Lamb, David, H., et al., Physico-Chemical Proc. Char. of Vaccines, Dev. Biol., Krager, 2000, vol. 103, pp. 251-258, Brown F., Corbel M., Griffiths E., (eds).
Lei, Q., P., et al., Physico-Chemical Proc. Char. of Vaccines, Dev. Biol., Krager, 2000, vol. 103, pp. 259-264, Brown F., Corbel M., Griffiths E., (eds).
Lindberg, Alf, A., C.R. Acad. Sci., Paris Sciences de la vie, 322:925-932 (1999).
MMWR, Recommendations and Reports, CDC, 49, No. RR-7, pp. 1, 6, 7(2000).
Perkins, Bradley, A., J. Amer. Med. Assoc., 283:2842-2843 (2000).
Plotkin, Stanley, A., and Orenstein, Walter, A., Vaccines 3rd Ed., W.B. Saunders Company, Philadelphia, PA, pp. 722-723 (1999).
Frasch, et al., Review of Infectious Diseases, 7:504-510 (1985).
Reido, et al., Pediatric Infectious Disease Journal, 14:643-657 (1995).

(56) References Cited

OTHER PUBLICATIONS

Artenstein, MS, et al., The New England Journal of Medicine, 282:417-420 (1970).
Peltola, et al., The New England Journal of Medicine, 297:686-691 (1997).
Reingold, et al., The Lancet, 2:114-118 (1985).
Goldschneider, et al., The Journal of Infectious Diseases, 128:769-776 (1973).
Gold, et al, The Journal of Infectious Diseases, 136:S21-S35 (1977).
Brandt, et al., The Journal of Infectious Diseases, 131:S69-S72 (1975).
Vaccines and Related Biological Products Advisory Committee; Notice of Meeting, Federal Register, vol. 64, No. 165, Aug. 26, 1999.
Prevention and Control of Meningococcal Disease and Meningococcal Disease and College Students, US Dept. of Health and Human Services, CDC, vol. 49, No. RR-7, Jun. 30, 2000.
Fusco, et al., "Meningococcal vaccine development: a novel approach," Expert Opinion on Investigational Drugs, pp. 245-252, Ashley Publications, ltd. 1998.
Zollinger et al., Abstracts of the Tenth International Pathogenic Neisseria Conference, Sep. 8-13, 1996, Baltimore, Maryland, USA.
Lindberg, Glycoprotein conjugate vaccines, Vaccine 17 (1999) S28-S36.
ACIP Charter http://www.cdc.gov/nip/ACIP/charter.htm.
Global Alliance for Vaccines and Immunization, Fourth Board meeting, The Netherlands, Nov. 19, 2000.
Meningococcal Conjugate Vaccine Development, Pasteur Merieux Connaught, Ryall Presentation for Sep. 15, 1999 meeting.
Transcript of Center for Biologics Education and Research, Vaccines and Related Biological Products Advisory committee meeting held Sep. 15, 1999.
Annex 1,Pfizer Inc's Opposition Statement against EP1355673 B1 Entitled "Multivalent meningococcal polysaccharide-protein conjugate vaccine" Apr. 8, 2013.
Observations Under Article 115 EPC, dated Apr. 5, 2011.
Rosenstein et al., "Update on Haemophilus Influenzae Serotype b and Meningococcal Vaccines," Pediatric Clinics of North America, v. 47:2: 337-352, Apr. 2000.
Merck Manual 17th Edition, 1999, p. 1097.
Declaration of Dennis L. Kasper, M.D. in support of Costantino Motion No. 5, p. 1-94, Doc. No. 181, filed Jul. 2, 2012 in Interference No. 105,830, Exhibit No. 2001.
Declaration of Dennis L. Kasper, M.D. in support of Costantino Substantive Motion 8, p. 1-28, Doc. No. 49, filed Mar. 8, 2012 in Interference No. 105,830, Exhibit No. 2011.
Declaration of Neil Ravenscroft, Ph.D. in support of Costantino Motion No. 5, p. 1-26, Doc. No. 189, filed Jul. 2, 2012 in Interference No. 105,830, Exhibit 2013.
Declaration of James A. Fiorato, in support of Substantive Costantino Motion No. 7, p. 1-19, Doc. No. 52, filed Mar. 8, 2012 in Interference No. 105,830, Exhibit 2030.
Declaration of Neil Ravenscroft, Ph.D. in support of Costantino Substantive Motion No. 7, p. 1-28, Doc. No. 64, filed Mar. 8, 2012 in Interference No. 105,830, Exhibit 2047.
Declaration of Dennis L. Kasper M.D. in support of Costantino's Opposition to Ryall Combined Motions 1 and 2, p. 1-30, Doc. No. 93, filed Apr. 26, 2012 in Interference No. 105,830, Exhibit 2071.
Robert Jones, Internet Forensics, "The Wayback Machine," p. 1-6, Doc. No. 95, filed Apr. 26, 2012 in Interference No. 105,830, Exhibit 2077.
Transcript of the Cross Examination of William Dick, Ph.D., given May 18, 2012, p. 1-72, Doc. No. 108, filed May 24, 2012 in Interference No. 105,830, Exhibit 2082.
Transcript of the Cross Examination of Evan H. Dygert, given May 18, 2012, p. 1-59, Doc. No. 109, filed May 24, 2012 in Interference No. 105,830, Exhibit 2083.
Declaration of Stephen I. Pelton, M.D., in support of Ryall's Combined Motions 1 and 2, Doc. 134, p. 1-14, filed Jun. 29, 2012 in Interference No. 105,830, Exhibit 1008.
Declaration of William Dick, in support of Ryall Opposition to Costantino's Motion No. 5, Doc. 84, p. 1-11, filed on Apr. 5, 2012 in Interference No. 105,830, Exhibit 1041.
Second Declaration of Stephen I. Pelton, M.D. in support of Ryall's Opposition to Costantino Motions 5, 7 and 8, Doc. No. 81, p. 1-14, filed Apr. 5, 2012 in Interference No. 105830, Exhibit 1042.
Declaration of Evan H. Dygert in Support of Ryall Opposition No. 7, Doc. No. 79, p. 1-9, filed Apr. 5, 2012 in Interference 105830, Exhibit 1045.
Description of NTFS date and time stamps for files and folders, http://support.microsoft.com/kb/299648, Doc. No. 78, p. 1-2, filed Apr. 5, 2012 in Interference No. 105830, Exhibit 1046.
File Name/File System Modified Date and Time for Ryall slides pdf, 1 page, Doc. No. 76, filed Apr. 5, 2012 in Interference No. 105830, Exhibit 1048.
www.fda.gov file system modified dates of webpages, Doc. 77, 1 page, filed Apr. 5, 2012 in Interference No. 105830.
Deposition transcript for William Dick, filed 00/29/12 in Interference No. 105830, Doc. 175, p. 1-72, Exhibit 1061.
Deposition transcript for Evan H. Dygert, filed 00/29/12 in Interference No. 105830, Doc. 176, p. 1-59, Exhibit 1062.
Declaration of Robert P. Ryall, p. 1-4, doc. 249, filed Nov. 29, 2012 in Interference No. 105830, Exhibit 1064.
Second declaration of Evan H. Dygert, p. 1-12, doc. 250, filed Nov. 29, 2012 in Interference No. 105830, Exhibit 1065.
Attorney General FOIA guidelines, doc. 251, p. 1-3, filed Nov. 29, 2012 in Interference No. 105830, Exhibit 1066.
Abstract, Vaccines and Related Biological Products Advisory Committee Meeting, Robert Ryall, Sep. 15, 1999, Doc. 252, p. 1-2, filed Nov. 29, 2012 in Interference 105830, Exhibit 1067.
Declaration of Angie Bricco, doc. 254, p. 1-3, filed Nov. 29, 2012 in Interference No. 105830, Exhibit 1069.
European Commission Cost/Std Initiative, Report of the Expert Panel VIII, New vaccines, especially new combined Vaccines. R. Rappuoli, Vaccine 14(7): 691-700 (1996).
Herzenberg, L. et al., "Epitope-specific Regulation, I CarrierSpecific Induction of Suppresion for IgG Anti-Hapten Antibody Response." J. Exp. Med. 155:1730-1740, 1982.
Barrington, et al., "Non-Epitope-Specific Suppression of the Antibody Response to Haemophilus Influenzae Type b Conjugate Vaccines by Preimmunization with Vaccine Components," Infec. Immun. 61:432-438 (1993).
Eskola, J., et al., "Randomised trial of the effect of co-administration with acellular pertussis DPT vaccine on immunogenicity of Haemophilus Influenzae type b conjugate vaccine," Lancet, 348:1688-1692 (1996).
Dagan, R., et al., "Reduced Response to Multiple Vaccines Sharing Common Protein Epitopes that are administered simultaneously to Infants," Infec. and Immun. 66(5):2093-2098 (1998).
Greenberg, D.P., "Factors influencing the immunogenicity of a pneumococcal conjugate vaccine in infants," Pediatr. Res. 41:12A (Abstract 709), 1997.
Eskola, J., et al., "Combined vaccination of Haemophilus influenza type b conjugate and diptheria-tetanus-pertussis containing acellular pertussis," The Lancet 354:2063-2067 (1999).
Ruiz-Palacios, G.M., et al., "Immunogenicity and Safety of a Booster dose of the 10-valent Pneumococcal haemophilus Influenzae Protein D conjugate Vaccine Co-Administered with the Tetravalent Meningococcal Serogroups A,C, W, and Y Tetanus Toxoid Conjugate Vaccine in Toddlers: A Randomized Trial," Vaccine Reports 32(1):62-71 (2013).
Dagan, R., et al., "Glycoconjugate vaccines and immune interference: a review," Vaccine 28:5513-5525 (2010).
Fattom, et al., "Epitopic overload at the site of injection may result in suppression of the immune response to combined capsular polysaccharide conjugate vaccines" Vaccine, vol. 17:126-133 1999.
Burrage, et al., "Effect of Vaccination with Carrier Protein on Response to Meningococcal C conjugate vaccines and value of different immunoassays as predictors of protection," Infection and Immunity, vol. 70(9):4946-4954, 2002.

(56) References Cited

OTHER PUBLICATIONS

Reddin et al., "Bordetella pertussis fimbriae are effective carrier proteins in *Neisseria meningitidis* serogroup C conjugate vaccines," FEMS Immunology and Medical Microbiology, vol. 31:153-162, 2001.
Lei, et al., "Quantification of free polysaccharide in meningococcal polysaccharide-diptheria toxoid conjugate vaccines," Developments in Biologicals, vol. 103, pp. 259-264, Switzerland, 2000.
Lamb, et al., "Capillary electrophoretic analysis of meningococcal polysaccharide-diptheria toxoid conjugate vaccines," Developments in Biologicals, vol. 103, 2000, pp. 251-258, Switzerland.
Package insert for Menactra A,C,Y, W-135 diptheria toxoid vaccine licensed in U.S. Mar. 2011.
Package insert for Menveo A,C,Y, W-135 CRM 197 vaccine license in the U.S. Mar. 2011.
Richmond et al., "Meningococcal Serogroup C Conjugate Vaccine is Immunogenic in Infancy and Primes for Memory," J. Infect. Dis. 179:1569-1572 (1999) (downloaded from http://jid.oxfordjournals.org by guest on Nov. 14, 2011).
Richmond, Ability of 3 Different Meningococcal C Conjugate Vaccines to Induce Immunologic Memory after a Single Dose in UK toddlers, J. of Infect. Dis. (2001) 183-160-3.
First Conjugate Vaccine to Protect Infants against Group C meningococcal disease passes EU mutual recognition procedure for seven European countries, http://www.thefreelibrary.com/FIRST+CONJUGATE+VACCINE+PROTECT+PR Newswire Assn. LLC (2000).
Chiron's Meningitis C Vaccine Approved in UK, http://web.archive.org/web/20010211031610/http://www.shareholder.com/chiron/new, downloaded Nov. 11, 2011. Chiron Corp (2000).
Baxter receives approval for NEISVAC-C meningococcal vaccine in the United Kingdom, http://web.archive.org/web200012012233/http://www.baxter.com/utilities/news/release, downloaded Nov. 11, 2011. Baxter Int'l Inc. (2000).
ISR, IPER for PCT/US02/01963 Jul. 30, 2004.
NeisVac-C British national formulary, Meningococcal Vaccines, http://bnf.org/bnf/bnf/current/90296.htm, downloaded Nov. 14, 2011.
Meningitec, British National Formulary http://bnf.org/bnf/current/81773.htm, Nov. 11, 2011.
Menjugate, British National Formulary, http://bnf.org/bnf/current855.93.htm, Nov. 14, 2011.
Federal Advisory Committee Act, United States Code Service, 5 USCS Appx ss.10 (1999), Lexis.
Code of Federal Regulations, Food and Drugs, 21, parts 1-99. Office of the Federal Register, National Archives and Records Administration, Apr. 1, 1999.
Artenstein, M.S., et al., Bulletin of the WHO 45:283-286 (1971).
MacDonald, N. E., et al., JAMA 280(19): 1686-1689 (1998).
Maslanka, S.E., et al., Infection and Immunity 66(6): 2453-2459 (1998).
F.D.A., Guidance for Industry: Providing Clinical Evidence of Effectiveness for Human Drug and Biologic Products § 2(C)(1)(a) (1998).
International Conference on Harmonisation of Technical Requirements for Registration of Pharmaceuticals for Human Use, Clinical Investigation of Medicinal Products in the Pediatric Population § 2.4 (2000).
Center for Disease Control and Prevention, Morbidity and Mortality Weekly Report 34(18) 255-259 (May 10, 1985).
Gold, R., et al., J. Infectious Disease 140(5): 690-697 (1979).
Goldblatt, D., Journal of Medical Microbiology 47:563-567 (1998).
Lepow, M.L, et al., J.Pediatrics 106(2): 185-189 (1985).
Transcript of Record of VRBPAC Advisory Committee, Sep. 15, 1999.
Peltola, H., et al., Lancet 340:592-594 (1992).
Fairley, C.K., et al., J. Infectious Disease 174:1360-1363 (1996).
Leach, A., et al, J. Infectious Disease 175:200-204 (1997).
Borrow, R., et al., Epidemiology & Infection 124:427-432 (2000).
Costantino, P., et al., Vaccine 17:1251-1263 (1999).
Biologics Electronic Reading Room, http://www.fda.gov/AboutFDA/CentersOffices/OfficeofMedicalProductsandTobacco/CBER/ucm129132.htm.
Screen capture of CBER Reading Room webpage at http://www.fda.gov/ohrms/dockets/ac/99lbackgrd/3544b1.htm.
Screen capture of CBER Reading Room webpage at http://www.fda.gov/ohrms/dockets/ac/99/ backgrd/3544b1d.pdf.
Dean, J.L., U.S. General Services Administration, Public Access to Records: Memorandum for Committee Management Officers (Mar. 14, 2000).
Notes for Speakers at VRBPAC Meetings, Aug. 30, 1999.
Pink Sheet Article No. 00610290023, vol. 61, No. 29, Jul. 19, 1999.
Robbins, J.B, et al., Pure Applied Chemistry 71(5): 745-54 (1999).
MacLennan, J.M., et al., JAMA 283(21) 2795-2801 (2000).
Ullmer, J.B., et al., Nature Biotechnology 24(11):1377-1383 (2006).
Dellepiane, N., et al., Bulletin of the WHO 78(2):155-162 (2000).
Fritzell B. & Plotkin S., J. Pediatrics 121(3):355-362 (1992).
Schneerson, R., et al., J. Experimental Medicine 152:361-76 (1980).
Bystrický S., et al., Glycoconjugate J. 16:691-696 (1999).
Aventis Pasteur, Meningococcal (Groups A, C, Y and W-135) Polysaccharide Diphtheria Toxoid Conjugate Vaccine Menactra Product Information:1-10 (Jan. 2005).
Cadoz, M., et al., Vaccine 3:340-342 (1985).
Armand, J., et al., J. Biol. Standardization 10:335-339 (1982).
Anderson, E.L., et al., Infection & Immunity 62(8):3391-3395 (1994).
Lieberman, J.M., et al., JAMA 275(19):1499-1503 (1996).
Maslanka, S.E., et al., Clinical Diagnostic Lab. Immunology. 4(2):156-167 (1997).
Anderson, P.W., et al., J. Immunology 137(4):1181-1186 (1986).
Ravenscroft, N. & Feavers, I.M., Conjugate Vaccines, in Handbook of Meningococcal Disease, Infection Biology, Vaccination, Clinical Management (2006) pp. 343-369.
Granoff, DM., et al., Meningococcal Vaccines in Vaccines: 959-987 (4th Ed. 2004).
Borrow, R. et al., Epidemiology and Infection, 124:427-432 (2000).
Chu, C. et al., Infection and Immunity, 40(1):245-256 (1983).
Gorringe, A.R. et al., Meningococcal Vaccines: Methods and Protocols in 66 Methods in Molecular Medicine: 241-254 (2001).
Halsey, N.A., Clin. Infect. Dis. 33 (Suppl. 4):S312-318 (2001).
Screen capture of a web-based readout from the Wayback Machine accessed through http://archive.org/web/web.php on Apr. 26, 2012.
Public web links on fda.gov accessed Apr. 26, 2012.
Fax Transmittal of Dr. John J. Donnelly's Presentation Overheads from Michelle Sixta of Chiron to Carl Frasch of the Center for Biologics Evaluation and Research (CBER), dated Sep. 14, 1999.
Campbell, J.D. et al., J. Infect. Diseases 186:1848-51 (2002).
Gold, et al., Meningococcal infections. 2 field trial of group c meningococcal polysaccharide vaccine in 196901970, Bull WHO, 45:279-282 (1971).
U.S. Appl. No. 12/321,420.
U.S. Appl. No. 10/481,457.
International Patent Application No. PCT/IB02/03191.
GB Patent Application No. 0115176.0.
Hadler et al., "Active Immunization," Pediatric Infectious Diseases, Long, Pickering & Prober, eds., NewYork: Churchill & Livingstone, pp. 49-70, (1997).
Pelton SI, et al., Pediatr Infect Dis J, 26:468-472 (2007).
Moore MR, et al. J Infect Dis., 197:1016-1027 (2008).
Fattom, et al., Vaccine, 22:880-887 (2004).
Cryz et al., Microbial Pathogen, 6:75-80 (1989).
Crucell Jul. 18, 2006 Press Release http://cws.huginonline.com/C1/32631/PR/200607/1064252_5_5.html.
Sawyer, LA et al, Vaccine, 12:851-856 (1994).
Decker MD et al. Ann. NY Academy of Sci, 234-240 (1995).
Anderson EL et al, JAMA, 273:849-853 (1995).
Egan W. et al, JAMA, 273:888-889 (1995).
Goldscheiner I et al, J Exper Med, 129:1307-1326 (1969).
Tejedor JC et al, Pediat Infect Dis J, 26:1-7 (2007).
Schmitt HJ et al Clin Vaccine Immuno, 14:426-434 (2007).
Granoff et al, JAMA, 272:1116-1121(1994).
Dagan R et al, Infect Immun, 66:2093-2098 (1998).

(56) References Cited

OTHER PUBLICATIONS

Poolman J, et al. Clinical and Vaccine Immunology,18(2):327-336 (2011).
Granoff et al., Infect. Immun., 77:764-769 (2009).
Mcvey, Galvin and Olson, International Journal for Parasitology, 33(5-6):507-516 (2003).
Griffin, Advanced Drug Delivery Reviews, 54:851-861 (2002).
Jakobsen et al. Infect Immun, 71(5):2956-9 (2003).
McVernon et al., Arch. Dis. Child, 88:379-83 (2003).
McVernon et al., Pediatr. Infect. Dis. J., 22: 659-61 (2003).
Cohn, A et al., Clin Infect Dis, 50(2):184-91 (Jan. 15, 2010).
Report of the Committee on Infectious Diseases, American Academy of Pediatrics (AAP), 2003, Pickering, ed.
Agenda of VRBPAC Meeting on Sep. 14-15, 1999.
www.fda.gov/ohrms/dockets/ac/cber99.htm.
www.fda.gov/ohrms/dockets/ac/99/backgrd/3544b1d.pdf.
Kelly et al, JAMA, 294(23):3019-23 (Dec. 21, 2005).
MMWR (CDC) May 27, 2005 55 (RR07).
Peltola, New England Journal of Medicine, 297:686-691 (1977).
Artenstein MS, et al., NEJM, 282:417-420 (1970).
Schutze et al, J. Immunol, 135:2319-2322 (1985).
Lepow, M.L, et al., J. Infective Disease, 154(6):1033-1036 (1986).
Lindberg, A. A., Vaccine 17:S28-S36 (1999).
Verheul, A.F.M., et al., Microbiological Reviews, 57(1):34-49 (1993).
Appendix D-8: The Prospects for Immunizing Against *Neisseria meningitides*, In: New Vaccine Development Establishing Priorities; vol. II Diseases of Importance in Developing Countries, by Institute of Medicine, National Academy Press, Washington, D.C., pp. 251-266, 1986 (Appendix D-8).
Ravenscroft, N., et al., Vaccine 17:2802-2816 (1999).
Campagne, G., et al., Pediatric Infectious Disease J. 19(2): 144-150 (2000).
MacLennan, J., et al., J. Infectious Disease 187: 97-104 (2001).
International Conference on Harmonisation of Technical Requirements for Registration of Pharmaceuticals for Human Use, General Considerations for Clinical Trials (E8) § 3.1.4.3(c) (Jul. 17, 1997).

MULTIVALENT MENINGOCOCCAL POLYSACCHARIDE-PROTEIN CONJUGATE VACCINE

This application is a continuation of U.S. application Ser. No. 13/738,698, filed Jan. 10, 2013, now allowed, which is a divisional of U.S. application Ser. No. 10/054,638 filed Jan. 22, 2002, now allowed, which claims the benefit of U.S. provisional application No. 60/263,435, filed Jan. 23, 2001, the disclosure of each of which are incorporated herein by reference in their entirety.

BACKGROUND OF THE INVENTION

1. Field of the Invention

The present invention relates to the field of medicine generally, and more specifically to microbiology, immunology, vaccines and the prevention of infection by a bacterial pathogen by immunization.

2. Summary of the Related Art

*Neisseria meningitidis* is a leading cause of bacterial meningitis and sepsis throughout the world. The incidence of endemic meningococcal disease during the last thirty years ranges from 1 to 5 per 100,000 in the developed world, and from 10 to 25 per 100,000 in developing countries (Reido, F. X., et al. 1995). During epidemics the incidence of meningococcal disease approaches 1000 per 1000,000. There are approximately 2,600 cases of bacterial meningitis per year in the United States, and on average 330,000 cases in developing countries. The case fatality rate ranges between 10 and 20%.

Pathogenic meningococci are enveloped by a polysaccharide capsule that is attached to the outer membrane surface of the organism. Thirteen different serogroups of meningococci have been identified on the basis of the immunological specificity of the capsular polysaccharide (Frasch, C. E., et al. 1985). Of these thirteen serogroups, five cause the majority of meningococcal disease; these include serogroups A, B, C, W135, and Y. Serogroup A is responsible for most epidemic disease. Serogroups B, C, and Y cause the majority of endemic disease and localized outbreaks.

The human naso-oropharyngeal mucosa is the only known natural reservoir of *Neisseria meningitidis*. Colonization takes place both at the exterior surface of the mucosal cell and the subepithelial tissue of the nasopharynx. Carriage of meningococci can last for months. Spreading of meningococci occurs by direct contact or via air droplets. Meningococci become invasive by passing through the mucosal epithelium via phagocytic vacuoles as a result of endocytosis. Host defense of invasive meningococci is dependent upon complement-mediated bacteriolysis. The serum antibodies that are responsible for complement-mediated bacteriolysis are directed in large part against the outer capsular polysaccharide.

Vaccines based on meningococcal polysaccharide have been described which elicit an immune response against the capsular polysaccharide. These antibodies are capable of complement-mediated bacteriolysis of the serogroup specific meningococci. The meningococcal polysaccharide vaccines were shown to be efficacious in children and adults (Peltola, H., et al. 1977 and Artenstein, M. S., et. al. 1970), but the efficacy was limited in infants and young children (Reingold, A. L., et. al. 1985). Subsequent doses of the polysaccharide in younger populations elicited a weak or no booster response (Goldschneider, I., et. al. 1973 and Gold, R., et. al. 1977). The duration of protection elicited by the meningococcal polysaccharide vaccines is not long lasting, and has been estimated to be between 3 to 5 years in adults and children above four years of age (Brandt, B., et. al. 1975, Käyhty, H., et al. 1980, and Ceesay, S. J., et. al. 1993). For children from one to four years old the duration of protection is less than three years (Reingold, A. L., et. al. 1985).

Polysaccharides are incapable of binding to the major histocompatibility complex molecules, a prerequisite for antigen presentation to and stimulation of T-helper lymphocytes, i.e., they are T-cell independent antigens. Polysaccharides are able to stimulate B lymphocytes for antibody production without the help of T-helper lymphocytes. As a result of the T-independent stimulation of the B lymphocytes, there is a lack of memory induction following immunization by these antigens. The polysaccharide antigens are capable of eliciting very effective T-independent responses in adults, but these T-independent responses are weak in the immature immune system of infants and young children.

T-independent polysaccharide antigens can be converted to T-dependent antigens by covalent attachment of the polysaccharides to protein molecules ("carriers" or "carrier proteins"). B cells that bind the polysaccharide component of the conjugate vaccine can be activated by helper T cells specific for peptides that are a part of the conjugated carrier protein. The T-helper response to the carrier protein serves to augment the antibody production to the polysaccharide.

The serogroup B polysaccharide has been shown to be poorly to non-immunogenic in the human population (Wyle, F. A., et. al. 1972). Chemical attachment of this serogroup polysaccharide to proteins has not significantly altered the immune response in laboratory animals (Jennings, H. J., et. al. 1981). The reason for the lack of immune response to this serogroup polysaccharide is thought to arise from structural similarities between the serogroup B polysaccharide and polysialylated host glycoproteins, such as the neural cell adhesion molecules.

A meningococcal conjugate vaccine based on serogroup C polysaccharide has been described. This monovalent vaccine elicits a strong functional antibody response to the capsular polysaccharide present on strains of *N. meningitidis* corresponding to serogroup C. Such a vaccine is only capable of protecting against disease caused by serogroup C bacteria.

Existing vaccines based on meningococcal polysaccharide are of limited use in young children and do not provide long-lasting protection in adults. The only meningococcal vaccine which as been shown to be capable of eliciting long-lasting protection in all groups, including children, at risk for meningococcal infection is based on a polysaccharide from a single serogroup of *N. meningitidis* and provides no protection against infection by other serogroups. Thus, a need exists for a meningococcal conjugate vaccine capable of conferring broad, long-lived protection against meningococcal disease in children and adults at risk for meningococcal infection. The multivalent meningococcal polysaccharides of the present invention solve this need by providing vaccine formulations in which immunogenic polysaccharides from the major pathogenic serogroups of *N. meningitidis* have been converted to T-dependent antigens through conjugations to carrier proteins.

SUMMARY OF THE INVENTION

The present invention provides immunological compositions for treatment of meningococcal polysaccharide-protein conjugates caused by pathogenic *Neisseria meningitidis.*

The present invention provides immunological compositions comprising two or more protein-polysaccharide conjugates, wherein each of the conjugates comprises a capsular polysaccharide from *N. meningitidis* conjugated to a carrier protein.

The present invention provides immunological compositions comprising two or more distinct protein-polysaccharide conjugates, wherein each of the conjugates comprises a capsular polysaccharide from a different serogroup of *N. meningitidis* conjugated to a carrier protein.

The present invention provides vaccines for meningococcal polysaccharide-protein conjugates caused by pathogenic *Neisseria meningitidis*. The present invention provides multivalent meningococcal vaccines comprised of immunologically effective amounts of from two to four distinct protein-polysaccharide conjugates, wherein each of the conjugates contains a different capsular polysaccharide conjugated to a carrier protein, and wherein each capsular polysaccharide is selected from the group consisting of capsular polysaccharide from serogroups A, C, W-135 and Y.

The present invention also provides methods of manufacture of a multivalent meningococcal polysaccharide-protein composition comprising purifying two or more capsular polysaccharides from pathogenic *Neisseria meningitidis*; conjugating the purified polysaccharides to one or more carrier proteins and combining the conjugates to make the multivalent meningococcal polysaccharide-protein composition.

The present invention further provides a method of inducing an immunological response to capsular polysaccharide of *N. meningitidis* comprising administering an immunologically effective amount of the immunological composition of the invention to a human or animal.

The present invention provides a multivalent meningococcal vaccine comprised of immunologically effective amounts of from two to four distinct protein-polysaccharide conjugates, wherein each of the conjugates contains a different capsular polysaccharide conjugated to a carrier protein, and wherein each capsular polysaccharide is selected from the group consisting of capsular polysaccharide from serogroups A, C, W-135 and Y.

The present invention provides a method of protecting a human or animal susceptible to infection from *N. meningitidis* comprising administering an immunologically effective dose of the vaccine of the invention to the human or animal.

All patents, patent applications, and other publications recited herein are hereby incorporated by reference in their entirety.

DETAILED DESCRIPTION OF THE INVENTION

The present invention comprises an immunological composition of two or more distinct protein-polysaccharide conjugates, wherein each of the conjugates comprises a capsular polysaccharide conjugated to a carrier protein. Thus, the present invention includes compositions that comprise two or more different capsular polysaccharides conjugated to one or more carrier protein(s).

Capsular polysaccharides can be prepared by standard techniques known to those of skill in the art (ref). In the present invention capsular polysaccharides prepared from serogroups A, C, W-135 and Y of *N. meningitidis* are preferred.

In a preferred embodiment, these meningococcal serogroup conjugates are prepared by separate processes and formulated into a single dosage formulation. For example, capsular polysaccharides from serogroups A, C, W-135 and Y of *N. meningitidis* are separately purified.

In a preferred embodiment of the present invention the purified polysaccharide is depolymerized and activated prior to conjugation to a carrier protein. In a preferred embodiment of the present invention capsular polysaccharides of serogroups A, C, W-135, and Y from *N. meningitidis* are partially depolymerized using mild oxidative conditions.

The depolymerization or partial depolymerization of the polysaccharides may then be followed by an activation step. By "activation" is meant chemical treatment of the polysaccharide to provide chemical groups capable of reacting with the carrier protein. A preferred activation method involves treatment with adipic acid dihydrazide in physiological saline at pH 5.0±0.1 for approximately two hours at 15 to 30° C. One process for activation is described in U.S. Pat. No. 5,965,714.

Once activated, the capsular polysaccharides may then be conjugated to one or more carrier proteins. In a preferred embodiment of the present invention each capsular polysaccharide is separately conjugated to a single carrier protein species. In a preferred embodiment the capsular polysaccharides from serogroups A, C, W-135 and Y of *N. meningitidis* are each separately conjugated to the same carrier protein species.

Carrier proteins may include inactivated bacterial toxins such as diphtheria toxoid, CRM197, tetanus toxoid, pertussis toxoid, *E. coli* LT, *E. coli* ST, and exotoxin A from *Pseudomonas aeruginosa*. Bacterial outer membrane proteins such as, outer membrane complex c (OMPC), porins, transferrin binding proteins, pneumolysis, pneumococcal surface protein A (PspA), or pneumococcal adhesin protein (PsaA), could also be used. Other proteins, such as ovalbumin, keyhole limpit hemocyanin (KLH), bovine serum albumin (BSA) or purified protein derivative of tuberculin (PPD) may also be used as carrier proteins. Carrier proteins are preferably proteins that are non-toxic and non-reactogenic and obtainable in sufficient amount and purity. Carrier proteins should be amenable to standard conjugation procedures. In a preferred embodiment of the present invention diphtheria toxin purified from cultures of *Corynebacteria diphtheriae* and chemically detoxified using formaldehyde is used as the carrier protein.

After conjugation of the capsular polysaccharide to the carrier protein, the polysaccharide-protein conjugates may be purified (enriched with respect to the amount of polysaccharide-protein conjugate) by a variety of techniques. One goal of the purification step is to remove the unbound polysaccharide from the polysaccharide-protein conjugate. One method for purification, involving ultrafiltration in the presence of ammonium sulfate, is described in U.S. Pat. No. 6,146,902. Alternatively, conjugates can be purified away from unreacted protein and polysaccharide by any number of standard techniques including, inter alia, size exclusion chromatography, density gradient centrifugation, hydrophobic interaction chromatography or ammonium sulfate fractionation. See, e.g., P. W. Anderson, et. al. (1986). J. Immunol. 137: 1181-1186. See also H. J. Jennings and C. Lugowski (1981) J. Immunol. 127: 1011-1018.

After conjugation of the polysaccharide and carrier protein the immunological compositions of the present invention are made by combining the various polysaccharide-protein conjugates. The immunological compositions of the present invention comprise two or more different capsular polysaccharides conjugated to one or more carrier protein(s). A preferred embodiment of the present invention is a bivalent immunological composition comprising capsular polysaccharides from serogroups A and C of *N. meningitidis* separately conjugated to diphtheria toxoid. More preferably the present invention is a tetravalent immunological composition comprising capsular polysaccharides from serogroups A, C, W-135 and Y of *N. meningitidis* separately conjugated to diphtheria toxoid.

Preparation and use of carrier proteins, and a variety of potential conjugation procedures, are well known to those skilled in the art. Conjugates of the present invention can be prepared by such skilled persons using the teachings contained in the present invention as well as information readily available in the general literature. Guidance can also be obtained from any one or all of the following U.S. patents, the teachings of which are hereby incorporated in their entirety by reference: U.S. Pat. Nos. 4,356,170; 4,619,828; 5,153,312; 5,422,427 and 5,445,817.

The immunological compositions of the present invention are made by separately preparing polysaccharide-protein conjugates from different meningococcal serogroups and then combining the conjugates. The immunological compositions of the present invention can be used as vaccines. Formulation of the vaccines of the present invention can be accomplished using art recognized methods. The vaccine compositions of the present invention may also contain one or more adjuvants. Adjuvants include, by way of example and not limitation, aluminum adjuvants, Freund's Adjuvant, BAY, DC-chol, pcpp, monophoshoryl lipid A, CpG, QS-21, cholera toxin and formyl methionyl peptide. See, e.g., Vaccine Design, the Subunit and Adjuvant Approach, 1995 (M. F. Powell and M. J. Newman, eds., Plenum Press, NY). The adjuvant is preferably an aluminum adjuvant, such as aluminum hydroxide or aluminum phosphate.

As demonstrated below, the vaccines and immunological compositions according to the invention elicit a T-dependent-like immune response in various animal models, whereas the polysaccharide vaccine elicits a T-independent-like immune response. Thus, the compositions of the invention are also useful research tools for studying the biological pathways and processes involved in T-dependent-like immune responses to *N. meningitidis* antigens.

The amount of vaccine of the invention to be administered a human or animal and the regime of administration can be determined in accordance with standard techniques well known to those of ordinary skill in the pharmaceutical and veterinary arts taking into consideration such factors as the particular antigen, the adjuvant (if present), the age, sex, weight, species and condition of the particular animal or patient, and the route of administration. In the present invention, the amount of polysaccharide-protein carrier to provide an efficacious dose for vaccination against *N. meningitidis* can be from between about 0.02 µg to about 5 µg per kg body weight. In a preferred composition and method of the present invention the dosage is between about 0.1 µg to 3 µg per kg of body weight. For example, an efficacious dosage will require less antibody if the post-infection time elapsed is less since there is less time for the bacteria to proliferate. In like manner an efficacious dosage will depend on the bacterial load at the time of diagnosis. Multiple injections administered over a period of days could be considered for therapeutic usage.

The multivalent conjugates of the present invention can be administered as a single dose or in a series (i.e., with a "booster" or "boosters"). For example, a child could receive a single dose early in life, then be administered a booster dose up to ten years later, as is currently recommended for other vaccines to prevent childhood diseases.

The booster dose will generate antibodies from primed B-cells, i.e., an anamnestic response. That is, the multivalent conjugate vaccine elicits a high primary (i.e., following a single administration of vaccine) functional antibody response in younger populations when compared to the licensed polysaccharide vaccine, and is capable of eliciting an anamnestic response (i.e., following a booster administration), demonstrating that the protective immune response elicited by the multivalent conjugate vaccine of the present invention is long-lived.

Compositions of the invention can include liquid preparations for orifice, e.g., oral, nasal, anal, vaginal, peroral, intragastric, mucosal (e.g., perlinqual, alveolar, gingival, olfactory or respiratory mucosa) etc., administration such as suspensions, syrups or elixirs; and, preparations for parenteral, subcutaneous, intradermal, intramuscular, intraperitoneal or intravenous administration (e.g., injectable administration), such as sterile suspensions or emulsions. Intravenous and parenteral administration are preferred. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", $17^{th}$ edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions that may be buffered to a selected pH. If digestive tract absorption is preferred, compositions of the invention can be in the "solid" form of pills, tablets, capsules, caplets and the like, including "solid" preparations which are time-released or which have a liquid tilling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size.

Liquid preparations are normally easier to prepare than gels, other viscous compositions, and solid compositions. Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage for (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active ingredient. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative can be employed to increase the shelf life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the *N. meningitidis* polysaccharide-protein carrier conjugates.

The invention will be further described by reference to the following illustrative, non-limiting examples setting forth in detail several preferred embodiments of the inventive concept. Other examples of this invention will be apparent to those skilled in the art without departing from the spirit of the invention.

EXAMPLES

Example 1

Preparation of *Neisseria Meningitidis* Serogroups A, C, W-135, and Y Purified Capsular Polysaccharides Powders Crude Paste Preparation Separately, *Neisseria meningitidis* serogroup A, C, W135, and Y wet frozen seed cultures were thawed and recovered with the aid of liquid Watson Scherp medium and planted in Blake bottles containing Mueller Hinton agar medium. The Blake were incubated at 35 to 37° C. in a $CO_2$ atmosphere for 15 to 19 hours. Following the incubation period, the growth from the Blake bottles were dislodged and added to 4 L flasks containing Watson Scherp medium. The flasks were incubated at 35 to 37° C. for 3 to 7 hours on a platform shaker. The contents of the 4 L flasks were transferred to a fermenter vessel containing Watson Scherp medium. The fermenter vessel was incubated at 35 to 37° C. for 7 to 12 hours controlling dissolved oxygen content and pH with supplement feed and antifoam additions. After the incubation period, the contents of the fermentor vessel were transferred to a 500 L tank, Cetavlon was added, and the material mixed for 1 hours. The Cetavlon treated growth was centrifuged at approximately 15,000 to 17,000×g at a flow rate of approximately 30 to 70 liters per hours. The crude polysaccharide was precipitated from the supernatant with a second Cetavlon precipitation. Cetavlon was added to the supernatant and the material mixed for at least 1 hour at room temperature. The material was stored at 1 to 5° C. for 8 to 12 hours. The precipitated polysaccharide was collected centrifugation at approximately 45,000 to 50,000×g at a flow rate of 300 to 400 ml per minute. The collected paste was stored at −60° C. or lower until further processed.

Purified Polysaccharide Powder Preparation

The inactivated paste was thawed and transferred to a blender. The paste was blended with 0.9M calcium chloride to yield a homogeneous suspension. The suspension was centrifuged at approximately 10,000×g for 15 minutes. The supernatant was decanted through a lint free pad into a container as the first extract. A second volume of 0.9M calcium chloride was added to the paste, and blended to yield a homogeneous suspension. The suspension was centrifuged as above, and the supernatant combined with the supernatant from the first extraction. A total of four extractions were performed, and the supernatants pooled. The pooled extracts were concentrated by ultrafiltration using 10-30 kDA MWCO spiral would ultrafiltration units.

Magnesium chloride was added to the concentrated, and the pH adjusted to 7.2 to 7.5 using sodium hydroxide. DNase and RNase were added to the concentrate, and incubated at to 28° C. with mixing for 4 hours. Ethanol was added to a concentration of 30 to 50%. Precipitated nucleic acid and protein were removed by centrifugation at 10,000×g for 2 hours. The supernatant was recovered and the polysaccharide precipitated by adding ethanol to 80% and allowing it to stand overnight at 1 to 5° C. The alcohol was siphoned off, and the precipitated polysaccharide was centrifuged for 5 minutes at 10,000×g. The precipitated polysaccharide was washed with alcohol. The polysaccharide was washed with acetone, centrifuged at 15 to 20 minutes at 10,000×g. The polysaccharide was dried under vacuum. The initial polysaccharide powder was dissolved into sodium acetate solution. Magnesium chloride was added and the pH adjusted to 7.2 to 7.5 using sodium hydroxide solution. DNase and RNase were added to the solution and incubated at 25 to 28° C. with mixing for 4 hours to remove residual nucleic acids. After incubation with these enzymes, an equal volume of sodium acetate-phenol solution was added to the polysaccharide-enzyme mixture, and placed on a platform shaker at 1 to 5° C. for approximately 30 minutes. The mixture was centrifuged at 10,000×g for 15 to 20 minutes. The upper aqueous layer was recovered and saved. An equal volume of sodium acetate-phenol solution was added to the aqueous layer, and extracted as above. A total of four extractions were performed to remove protein and endotoxin from the polysaccharide solution. The combined aqueous extracts were diluted up to ten fold with water for injection, and diafiltered against 10 volumes of water for injection. Calcium chloride was added to the diafiltered polysaccharide. The polysaccharide was precipitated overnight at 1 to 50 C by adding ethanol to 80%. The alcohol supernatant was withdrawn, and the polysaccharide collected by centrifugation at 10,000×g for 15 minutes. The purified polysaccharide was washed two times with ethanol, and once with acetone. The washed powder was dried under vacuum in a desiccator. The dried powder was stored at −30° C. or lower until processed onto conjugate.

Example 2

Depolymerization of *Neisseria meningitidis* Serogroups A, C, W135, and Y Purified Capsular Polysaccharide Powder Materials used in the preparation include purified capsular polysaccharide powders from *Neisseria meningitidis* serogroups A, C, W-135, and Y (prepared in accordance with Example 1), sterile 50 mM sodium acetate buffer, pH 6.0, sterile 1N hydrochloric acid, sterile 1N sodium hydroxide, 30% hydrogen peroxide, and sterile physiological saline (0.85% sodium chloride).

Each serogroup polysaccharide was depolymerized in a separate reaction. A stainless steel tank was charged with up to 60 g of purified capsular polysaccharide powder. Sterile 50 mM sodium acetate buffer, pH 6.0 was added to the polysaccharide to yield a concentration of 2.5 g polysaccharide per liter. The polysaccharide solution was allowed to mix at 1 to 5° C. for 12 to 24 hours to effect solution. The reaction tank was connected to a heat exchanger unit. Additional 50 mM sodium acetate buffer, pH 6.0, was added to dilute the polysaccharide to reaction concentration of 1.25 g per liter. The polysaccharide solution was heated to 55° C.±0.1. An aliquot of 30% hydrogen peroxide was added to the reaction mixture to yield a reaction concentration of 1% hydrogen peroxide.

The course of the reaction was monitored by following the change in the molecular size of the polysaccharide over time. Every 15 to 20 minutes, aliquots were removed from the reaction mixture and injected onto a HPSEC column to measure the molecular size of the polysaccharide. When the molecular size of the polysaccharide reached the targeted molecular size, the heating unit was turned off and the polysaccharide solution rapidly cooled to 5° C. by circulation through an ice water bath. The depolymerized polysaccharide solution was concentrated to 15 g per liters by connecting the reaction tank to an ultrafiltration unit equipped with 3000 MWCO regenerated cellulose cartridges. The concentrated depolymerized polysaccharide solution was diafiltered against 10 volumes of sterile physiological saline (0.85% sodium chloride). The depolymerized polysaccharide was stored at 1 to 5° C. until the next process step.

The molecular size of the depolymerized polysaccharide was determined by passage through a gel filtration chromatography column sold under the tradename "Ultahydrogel™ 250" that was calibrated using dextran molecular size standards and by multi-angle laser light scattering. The quantity of polysaccharide was determined by phosphorus content for serogroup A using the method of Bartlet, G. R. J. (1959) Journal of Biological Chemistry, 234, pp-466-468, and by the sialic acid content for serogroups C, W135 and Y using the method of Svennerholm, L. (1955) Biochimica Biophysica Acta 24, pp 604-611. The O-acetyl content was determined by the method of Hesterin, S. (1949) Journal of Biological Chemistry 180, p 249. Reducing activity was determined by the method of Park, J. T. and Johnson, M. J. (1949 Journal of Biological Chemistry 181, pp 149-151. The structural integrity of the depolymerized polysaccharide was determined by protein $^1$H and $^{13}$C NMR. The purity of the depolymerized polysaccharide was determined by measuring the LAL (endotoxin) content and the residual hydrogen peroxide content.

Example 3

Derivatization of *Neisseria Meningitidis* Serogroups A, C, W-135, and Y Depolymerized Polysaccharide Materials used in this preparation include hydrogen peroxide depolymerized capsular polysaccharide serogroups A, C, W-135, and Y from *Neisseria meningitidis* (prepared in accordance with Example 2), adipic acid dihydrazide, 1-ethyl-3-(3-dimethylaminopropyl) carbodiimide (EDAC) for serogroup A only, sodium cyanoborohydride, sterile 1N hydrochloric acid, sterile 1N sodium hydroxide, sterile 1M sodium chloride, and sterile physiological saline (0.85% sodium chloride).

Each serogroup polysaccharide was derivatized in a separate reaction. A stainless steel tank was charged with the purified depolymerized polysaccharide, and diluted with sterile 0.85% physiological saline to achieve a final reaction concentration of 6 g polysaccharide per liter. To this solution was added a concentrated aliquot of adipic acid dihydrazide dissolved in sterile 0.85% physiological saline, in order to achieve a reaction concentration of 1 g per liter. For serogroup A only, EDAC was added as a concentrated aliquot dissolved in sterile 0.85% physiological saline, to achieve a reaction concentration of 1 g per liter. The pH was adjusted to 5.0±0.1, and this pH was maintained for 2 hours using sterile 1N hydrochloric acid and sterile 1N sodium hydroxide at room temperature (15 to 30° C.). After two hours, a concentrated aliquot of sodium cyanoborohydride, dissolved in 0.85% physiological saline, was added to the reaction mixture to achieve a reaction concentration of 2 g per liter. The reaction was stirred at room temperature (15 to 30° C.) for 44 hours±4 hours while maintaining the pH at 5.5±0.5. Following this reaction period, the pH was adjusted to 6.0±0.1, and the derivatized polysaccharide was concentrated to 12 g polysaccharide per liter by connecting the reaction tank to a ultrafiltration unit equipped with a 3000 MWCO regenerated cellulose cartridges. The concentrated derivatized polysaccharide was diafiltered against 30 volumes of 1M sodium chloride, followed by 10 volumes of 0.15M sodium chloride. The tank was disconnected from the ultrafiltration unit and stored at 1 to 5° C. for 7 days. The tank was reconnected to an ultrafiltration unit equipped with 3000 MWCO regenerated cellulose cartridges, and diafiltered against 30 volumes of 1M sodium chloride, followed by volumes of 0.15M sodium chloride.

The molecular size of the derivatized polysaccharide, the quantity of polysaccharide, and the O-acetyl content were measured by the same methods used on the depolymerized polysaccharide. The hydrazide content was measured by the 2,4,6-trinitrobenzensulfonic acid method of Snyder, S. L. and Sobocinski, P. Z. (1975) Analytical Biochemistry 64, pp 282-288. The structural integrity of the derivatized polysaccharide was determined by proton $^1$H and $^{13}$C NMR. The purity of the derivatized polysaccharide was determined by measuring the level of unbound hydrazide, the LAL (endotoxin) content, and the residual cyanoborohydride content.

Example 4

Preparation of Carrier Protein

Preparation of Crude Diphtheria Toxoid Protein

Lyophilized seed cultures were reconstituted and incubated for 16 to 18 hours. An aliquot from the culture was transferred to a 0.5-liter flask containing growth medium, and the culture flask was incubated at 34.5 to 36.5° C. on a rotary shaker for 7 to 9 hours. An aliquot from the culture flask was transferred to a 4-liter flask containing growth medium, and the culture flask was incubated at 34.5 to 36.5° C. on a rotary shaker for 14 to 22 hours. The cultures from the 4-liter flask were used to inoculate a fermenter containing growth media. The fermenter was incubated at 34.5 to 36.5° C. for 70 to 144 hours. The contents of the fermenter were filtered through depth filters into a collection vessel. An aliquot of formaldehyde solution, 37% was added to the harvest to achieve a concentration of 0.2%. The pH was adjusted to 7.4 to 7.6. The harvest was filtered through a 0.2 micron filter cartridge into sterile 20 liter bottles. The bottles were incubated at 34.5 to 36.5° C. for 7 days. An aliquot of formaldehyde solution, 37%, was added to each 20 liter bottle to achieve a concentration of 0.4%. The pH of the mixtures was adjusted to 7.4 to 7.6. The bottles were incubated at 34.5 to 36.5° C. for 7 days on a shaker. An aliquot of formaldehyde solution, 37%, was added to each 20 liter bottle to achieve a concentration of 0.5%. The pH of the mixtures was adjusted to 7.4 to 7.6. The bottles were incubated at 34.5 to 36.5° C. for 8 weeks. The crude toxoid was tested for detoxification. The bottles were stored at 1 to 5° C. during the testing period.

Purification of the Crude Diphtheria Toxoid Protein

The crude toxoid was allowed to warm to room temperature, and the contents of the 20-liter bottles were combined into a purification tank. The pH of the toxoid was adjusted to 7.2 to 7.4, and charcoal was added to the crude toxoid and mixed for 2 minutes. The charcoal toxoid mixture was allowed to stand for 1 hours, and was then filtered through a depth filter cartridge into a second purification tank. Solid ammonium sulfate was added to the filtrate to achieve 70% of saturation. The pH was adjusted to 6.8 to 7.2, and the solution was allowed to stand for 16 hours. The precipitated protein was collected by filtration and washed with 70% of saturation ammonium sulfate solution, pH 7.0. The precipitate was dissolved into sterile distilled water, and the protein solution was filtered into a stainless steel collection vessel. The pH was adjusted to 6.8 to 7.2, and ammonium sulfate was added to 40% of saturation. The pH of the solution was adjusted to 7.0 to 7.2, and the solution was allowed to stand for 16 hours. The precipitate was removed by filtration and discarded. Ammonium sulfate was added to the filtrate to 60% of saturation, and the pH adjusted to 7.0 to 7.2. The mixture was allowed to stand for 16 hours, and the precipitated protein was collected by filtration. The precipitate was dissolved into sterile distilled water, filtered to remove undissolved protein, and diafiltered against 0.85% physiological saline.

Concentration and Sterile Filtration of the Purified Diphtheria Toxoid Protein

The protein solution was concentrated to 15 g per liter and diafiltered against 10 volumes of 0.85% physiological saline suing a 10,000 MWCO regenerated cellulose filter cartridge. The concentrated protein solution was sterilized by filtration through a 0.2 micron membrane. The protein solution was stored at 1 to 5° C. until processed onto conjugate.

The protein concentration was determined by the method of Lowry, O. H. et. al (1951) Journal of Biological Chemistry 193, p 265-275. The purity of the protein was measured by sterility, LAL (endotoxin) content, and residual formaldehyde content.

Example 5

Preparation of Monovalent Conjugates of *Neisseria Meningitidis* Serogroups A, C, W-135, and Y Polysaccharide to Diphtheria Toxoid Protein Materials used in this preparation include adipic acid derivatized polysaccharide from *Neisseria meningitidis* serogroups A, C, W-135, and Y (prepared in accordance with Example 3), sterile diphtheria toxoid protein (prepared in accordance with Example 4), EDAC, ammonium sulfate, sterile 1N hydrochloric acid, sterile 1N sodium hydroxide, and sterile physiological saline (0.85%).

Each serogroup polysaccharide conjugate was prepared by a separate reaction. All four conjugates were prepared by the following process. A stainless steel tank was charged with the purified adipic acid derivatized polysaccharide at a reaction concentration of 700 to 100 µmoles of reactive hydrazide per liter and purified diphtheria toxoid protein at a reaction concentration of 3.8 to 4.0 g protein per liter. Physiological saline 0.85%, was used to dilute the starting materials to the target reaction concentrations and the pH was adjusted to 5.0±0.1.

An aliquot of EDAC was added to the polysaccharide protein mixture to achieve a reaction concentration of 2.28 to 2.4 g per liter. The pH of the reaction was kept at 5.0±0.1 for 2 hours at 15 to 30° C. After two hours, the pH was adjusted to 7.0±0.1 using sterile 1N sodium hydroxide, and the reaction was stored at 1 to 5° C. for 16 to 20 hours.

The reaction mixture was allowed to warm to 15 to 30° C. and the reaction vessel was connected to an ultrafiltration unit equipped with a 30,000 MWCO regenerated cellulose cartridge. Solid ammonium sulfate was added to 60% of saturation (for serogroups A, W-135 and Y) and 50% of saturation (for serogroup C). The conjugate reaction mixture was diafiltered against volumes of 60% of saturated ammonium sulfate solution (for serogroups A, W-135 and Y) and 50% of saturated ammonium sulfate solution (for serogroup C), followed by 20 volumes of physiological saline, 0.85%. The diafiltered conjugate was first filtered through a filter capsule containing a 1.2 micron and a 0.45 micron filter, and then through a second filter capsule containing a 0.22 micron filter.

The quantity of polysaccharide and O-acetyl content were measured by the same methods used on the depolymerized and derivatized polysaccharide. The quantity of protein was determined by the Lowry method. The molecular size of the conjugate was determined by passage through a gel filtration chromatography column sold under the tradename "TSK6000PW" that used DNA as the void volume marker, ATP as the total volume marker, and bovine thyroglobulin as a reference marker. In addition, the molecular size of the conjugate eluted from the TKS6000PW column was measured by multi-angle laser light scattering. The antigenic character of the conjugate was measured by binding to anti-polysaccharide serogroup specific antibody using double-sandwich ELISA method. The purity of the conjugates was determined by measuring the amount of unbound (unconjugated) polysaccharide by elution though a hydrophobic interaction chromatography column, unconjugated protein by capillary electrophoresis, sterility, LAL (endotoxin) content, residual EDAC content, and residual ammonium ion content.

Example 6

Formulation of a Multivalent Meningococcal A, C, W-135, and Y Polysaccharide Diphtheria Toxoid Conjugate Vaccine Materials used in this preparation include, serogroups A, C, W-135, and Y polysaccharide-diphtheria toxoid conjugates (prepared in accordance with Example 5), sterile 100 mM sodium phosphate buffered physiological saline (0.85% sodium chloride).

An aliquot of sterile 100-500 mM sodium phosphate buffered physiological saline was added to physiological saline (0.85%) in a stainless steel bulking tank to yield a final vaccine concentration of 10 mM sodium phosphate. An aliquot of each of from two to four of the sterile monovalent meningococcal polysaccharide-diphtheria toxoid conjugates was added to the bulking tank containing 10 mM sterile sodium phosphate physiological saline to yield a final concentration of 8 µg of each serogroup polysaccharide per milliliter of buffer. The formulated tetravalent conjugate was mixed and filtered through a 0.2 µm filter into a second bulking tank.

The quantity of each serogroup polysaccharide present in the multivalent formulation was determined by component saccharide analysis using high pH anion-exchange chromatography with pulsed amperometric detection. The quantity of protein was measured by the method of Lowry. The pH of the vaccine was measured using a combination electrode connected to a pH meter. The antigenic character of the multivalent conjugate vaccine was measured by binding to anti-polysaccharide serogroup specific antibody using a double-sandwich ELISA method. Immunogenicity of the multivalent conjugate vaccine was measured the ability of each conjugate present in the vaccine to elicit both a primary and booster anti-polysaccharide IgG immune response in an animal model. The purity of the multivalent conjugate vaccine was determined by measuring the amount of unbound (unconjugated) polysaccharide using high pH anion-exchange chromatography with pulsed amperometric detection, sterility, LAL (endotoxin) content, pyrogenic content, and general safety.

Example 7

Preparation of Aluminum-Hydroxide Adjuvanted Multivalent Meningococcal Polysaccharide Diphtheria Toxoid Protein Conjugate Preparation of conjugate adsorbed to aluminum hydroxide. Materials used in this preparation include serogroups A, C, W-135, and Y polysaccharide-diphtheria toxoid conjugates preparation described in Example 5, sterile physiological saline (0.85% sodium chloride), and sterile aluminum hydroxide in physiological saline (0.85% sodium chloride).

An aliquot of each of the sterile monovalent meningococcal polysaccharide diphtheria toxoid conjugates was added to the bulking tank containing physiological saline to yield a final concentration of 8 µg of each serogroup polysaccharide per milliliter of buffer. An aliquot of sterile aluminum hydroxide in physiological saline (0.85% sodium chloride) was added to the multivalent conjugate vaccine to achieve a final concentration of 0.44 mg aluminum ion per milliliter vaccine.

Example 8

Preparation of Aluminum Phosphate-Adjuvanted Conjugate

Materials used in this preparation include serogroups A, C, W-135, and Y polysaccharide-diphtheria toxoid conjugates preparation described in Example 5, sterile physiological saline (0.85% sodium chloride), and sterile aluminum phosphate in physiological saline (0.85% sodium chloride).

An aliquot of each of the sterile monovalent meningococcal polysaccharide-diphtheria toxoid conjugates was added to the bulking tank containing physiological saline to yield a final concentration of 8µg of each serogroup polysaccharide per milliliter of buffer. An aliquot of sterile aluminum phosphate in physiological saline (0.85% sodium chloride) was added to the multivalent conjugate vaccine to achieve a final concentration of 0.44 mg aluminum ion per milliliter vaccine.

Example 9

Immunogenicity of the Tetravalent Conjugate Vaccine

The tetravalent conjugate vaccine was studied for its ability to elicit an immune response in small laboratory animals prior to evaluation in the clinic. Mice, rats and rabbits have been used to study the immunogenicity of conjugate vaccines relative to the polysaccharide vaccines. These animal models are useful, because they are capable of distinguishing the conjugate vaccine from the corresponding polysaccharide by their immune response pattern. The conjugate vaccine elicits a T-dependent-like immune response in these models, whereas the polysaccharide vaccine elicits a T-independent-like immune response.

In the mouse immunogenicity studies, the conjugate was diluted with physiological saline (0.85% sodium chloride) to administer between one-quarter to one-sixteenth of a human dose. The mice were administered one or two doses of vaccine, either conjugate or polysaccharide, and blood specimens were taken two weeks post vaccination. One group of mice served as an unimmunized control group. Antibodies to each of the serogroup polysaccharides were measured by an ELISA method. The serum samples were incubated with excess of each capsular polysaccharide that was bound to a ELISA microtiter plate well. Methylated human serum albumin was used to bind each serogroup polysaccharide to the microtiter well. Following incubation the microtiter well was washed with buffer, and a secondary antibody-enzyme conjugate was added to the antibody-polysaccharide complex which binds to the anti-meningococcal polysaccharide antibody. The microtiter plate was washed, and a chemical substrate was added to the polysaccharide-meningococcal antibody-secondary antibody-enzyme conjugate. The enzyme hydrolyzes a portion of the chemical substrate that results in color formation. The amount of color formation is proportional to the amount of polysaccharide-meningococcal antibody-secondary antibody-enzyme conjugate that is bound to the microtiter well. The potency of the vaccine was determined by comparison to reference antisera for each serogroup, which is measured in the same microtiter plate, by a parallel line calculation using a four-parameter fit. The mouse reference antisera was generated in the same strain of mice that were individually immunized with three doses of each serogroup conjugate vaccine. The mouse reference antisera were assigned titers based on the inverse of dilution yielding an optical density of 1.0.

Presented in Table 1 is a summary of anti-polysaccharide IgG titers for each serogroup achieved in Swiss-Webster mice who were vaccinated with two doses of either the tetravalent conjugate vaccine, both liquid and aluminum hydroxide formulation, or the corresponding tetravalent polysaccharide vaccine. The IgG titers were measured on pooled sera from a set of ten mice. Two sets of 10 mice were used to measure the immune response to each vaccine formulation. Both sets were vaccinated on day 1. On day 15 (2 weeks post vaccination) blood specimens were taken from one set of 10 mice, and the second set of ten mice were vaccinated with a second dose of vaccine on day 15. Two weeks late on day 29, blood specimens were taken from the second set of 10 mice, and from the unimmunized control group. All antibodies were titrated at the same time, that is, both the day 15 and day 29 blood specimens were assayed at the same time along with the unimmunized controls and the mouse reference sera.

TABLE 1

Anti-polysaccharide IgG titers on pooled sera from Swiss-Webster mice vaccinated with either tetravalent conjugate or polysaccharide.

| Vaccine Group | Dosage µg ps | Anti-Men A | | Anti-Men C | | Anti-Men W135 | | Anti-Men Y | |
|---|---|---|---|---|---|---|---|---|---|
| | | D15 | D29 | D15 | D29 | D15 | D29 | D15 | D29 |
| Conjugate (no adjuvant) | 0.25 | 131 | 2640 | 250 | 1510 | 1350 | 6100 | 5660 | 4830 |

TABLE 1-continued

Anti-polysaccharide IgG titers on pooled sera from Swiss-Webster mice vaccinated with either tetravalent conjugate or polysaccharide.

| Vaccine Group | Dosage µg ps | Anti-Men A D15 | Anti-Men A D29 | Anti-Men C D15 | Anti-Men C D29 | Anti-Men W135 D15 | Anti-Men W135 D29 | Anti-Men Y D15 | Anti-Men Y D29 |
|---|---|---|---|---|---|---|---|---|---|
| Conjugate (no adjuvant) | 0.50 | 171 | 6220 | 416 | 2050 | 849 | 26000 | 5980 | 112000 |
| Conjugate (no adjuvant) | 1.0 | 249 | 4500 | 525 | 2740 | 1450 | 16600 | 11300 | 59100 |
| Conjugate (Alum. Hyd.) | 0.25 | 2920 | 4500 | 1010 | 2980 | 2300 | 33700 | 11600 | 124000 |
| Conjugate (Alum. Hyd.) | 0.50 | 5800 | 9550 | 2280 | 1010 | 4810 | 71900 | 26400 | 330000 |
| Conjugate (Alum. Hyd.) | 1.0 | 6210 | 9350 | 2630 | 12800 | 7870 | 94000 | 32700 | 302000 |
| Polysaccharide (no adjuvant) | 1.0 | 136 | 173 | 184 | 205 | 612 | 608 | 4470 | 3910 |
| Unimmunized | n.a. | — | 110 | — | 145 | — | 623 | — | 777 |

The tetravalent conjugate vaccine, both unadjuvanted and adjuvanted with aluminum hydroxide, is capable of eliciting a strong anti-polysaccharide IgG immune response in this mouse model. The aluminum hydroxide adjuvant serves to improve both the primary and booster response to each of the four serogroup polysaccharide conjugates. The tetravalent polysaccharide vaccine elicits a negligible immune response to serogroups A, C, and W135 in this mouse model relative to the unimmunized control, whereas serogroup Y does elicit a respectable immune response, but not a booster response. The tetravalent polysaccharide vaccine fails to elicit a booster response to all four serogroup polysaccharides in this model. This model can readily differentiate between the polysaccharide vaccine and the conjugate vaccine both by the magnitude of the immune response and booster response pattern to each of the serogroup conjugate vaccines.

The unadjuvanted form of the tetravalent conjugate vaccine has been studied in the clinic for safety and immunogenicity in young healthy adults and in young healthy children. In the adult study, subjects were vaccinated with a single dose of vaccine, formulated to contain 4 µg of each of the four conjugates, as polysaccharide. Blood specimens were taken immediately prior to vaccination and 28-days post vaccination. Antibodies to each of the serogroup conjugates were measured by an ELISA measurement that quantified the amount of anti-polysaccharide IgG. The ELISA method is very similar to the method used to measure the amount if IgG antibody present in mouse sera.

Briefly, the serum samples were incubated in ELISA microtiter wells that were coated with excess meningococcal polysaccharide that was bound to the plate with methylated human serum albumin. The amount of bound antibody was determined by a reaction with peroxidase-labeled mouse anti-human IgG specific monoclonal antibody. A subsequent reaction using peroxidase substrate generates a chromogenic product that was measured spectrophotometrically. The resulting optical density of the chromophore correlates with the amount of IgG antibody in the serum that is bound to the meningococcal polysaccharide on the microtiter plate. The amount of antibody was calculated by comparison to a human reference sera (CDC 1922) with an assigned value using a 4-parameter logistic curve method. In addition, the antibodies were measured for their ability to lyse serogroup specific bacteria. The serum samples are first heat-inactivated to destroy complement. The serum samples are diluted by two-fold dilutions in a sterile 96-well microtiter plate. Serogroup specific bacteria along with baby rabbit complement were added to the serum dilutions and allowed to incubate. After an incubation period, an agar overlay medium was added to the serum/complement/bacteria mixture. The agar overlay was allowed to harden, and then incubated overnight at 37° C. with 5% carbon dioxide. The next day, bacterial colonies present in the wells were counted. The endpoint titer was determined by the reciprocal serum dilution yielding greater than 50% killing as compared to the mean of the complement control wells.

Presented in Table 2 is a summary of the anti-polysaccharide mean IgG concentrations for each serogroup and the mean serum bactericidal antibody (SBA) titer in adult sera pre and post vaccination with the tetravalent conjugate vaccine formulated at 4 µg polysaccharide per dose. The immune response to all four serogroup conjugates were satisfactory, that is comparable to the immune response achieved by the licensed polysaccharide vaccine in terms of both IgG antibody and functional bactericidal antibody responses. The vaccine was found to be safe for this age group and the safety profile was found to be similar to that of the licensed polysaccharide vaccine.

TABLE 2

Anti-polysaccharide IgG GMC (group mean concentration and Serum Bactericidal Antibody GMTs (group mean titers) for young health adults vaccinated with a tetravalent meningococcal conjugate vaccine formulated at 4 µg per dose by polysaccharide.

| Immune Response by Serogroup | $N_{pre}/N_{post}$ | IgG GMC (µg/ml) [95% CI] Pre | IgG GMC (µg/ml) [95% CI] Post | SBA GMT [95% CI] Pre | SBA GMT [95% CI] Post |
|---|---|---|---|---|---|
| A | 28/28 | 3.3 [2.3-4.8] | 38.4 [22.2-66.4] | 487 [231-1027] | 6720 [4666-15428] |

TABLE 2-continued

Anti-polysaccharide IgG GMC (group mean concentration and Serum Bactericidal Antibody GMTs (group mean titers) for young health adults vaccinated with a tetravalent meningococcal conjugate vaccine formulated at 4 µg per dose by polysaccharide.

| Immune Response by Serogroup | $N_{pre}/N_{post}$ | IgG GMC (µg/ml) [95% CI] | | SBA GMT [95% CI] | |
|---|---|---|---|---|---|
| | | Pre | Post | Pre | Post |
| C | 28/28 | 0.4 [0.2-0.7] | 5.5 [3.0-10.1] | 16.4 [7.1-37.7] | 1560 [800-4042] |
| W-135 | 28/28 | 0.6 [0.3-1.0] | 5.8 [2.9-11.7] | 10.0 [5.9-16.9] | 609 [250-1481] |
| Y | 28/28 | 1.3 [0.7-2.5] | 6.8 [3.2-14.6] | 19.0 [8.0-41.2] | 390 [143-1061] |

In younger age groups, children less than 2 years of age, the immune response to the polysaccharide vaccine is weak and the immunity has been estimated to wane after one year. Children 12 to 15 months of age were administered a single dose of tetravalent conjugate vaccine formulated at 4 µg of each serogroup polysaccharide per dose, and they were administered a second dose of tetravalent conjugate vaccine two months following the first dose. Blood specimens were taken prior to the first and second vaccination, and one month post the second vaccination. The antibody responses to the four serogroup conjugates are summarized in Table 3. For each serogroup a booster response for IgG antibody and for functional-bactericidal antibody was observed following a second dose of tetravalent conjugate. The level of IgG antibody elicited by the conjugate vaccine is comparable to that elicited by the licensed polysaccharide for this age group; a post 6 week response of 3.64 µg/ml (2.96-4.49) IgG antibody response to serogroup C polysaccharide. However, the level of bactericidal antibody elicited by the conjugate vaccine is much higher than what is normally elicited by the licensed polysaccharide vaccine for this age group; a post 6 week SBA titer of 7.2 (5.0-10.4). The reason for this discordance between IgG antibody and bactericidal antibody in the younger populations is thought to result from the polysaccharide eliciting a high proportion of low avidity antibody in the younger populations. Conversely, the conjugate appears to elicit a much higher proportion of high avidity antibody. High avidity antibody is thought to be responsible for the bactericidal activity.

In addition to the ability of the tetravalent conjugate vaccine to elicit a high functional antibody response in younger populations compared to the licensed polysaccharide vaccine, the tetravalent conjugate vaccine is capable of eliciting an anamnestic response, demonstrating that protection elicited by the tetravalent conjugate vaccine of the present invention is long-lived. In the development of the tetravalent conjugate vaccine, studies were first conducted on a bivalent AC conjugate formulation. The vaccine offers wider coverage than the current licensed monovalent C conjugate, but does not protect against disease caused by serogroups W135 and Y.

A clinical study was performed with infant subjects that compared the immune response to the bivalent AC polysaccharide vaccine versus the bivalent AC conjugate vaccine. In this study, a third group of infants were enrolled to serve as a control group and they received a Haemophilus influenzae type b conjugate. All three vaccine groups receive the same pediatric vaccines. The bivalent AC conjugate group received three doses of conjugate vaccine (4 µg polysaccharide per dose) at 6, 10, and 14 weeks of age. The bivalent AC polysaccharide group received two doses of a bivalent AC polysaccharide vaccine (50 µg polysaccharide per dose) at 10 and 14 weeks of age. The Haemophilus influenzae type b conjugate group received three doses of conjugate vaccine at 6, 10, and 14 weeks of age. Blood specimens were taken at 6 weeks, pre-vaccination, and at 18 weeks, 4 weeks post vaccination. When the children were 11 to 12 months of age, blood specimens were taken and the children who had received either the bivalent AC conjugate or the bivalent AC polysaccharide

TABLE 3

Anti-polysaccharide IgG GMC (group mean concentration) and Serum Bactericidal Antibody GMTs (group mean titers) for young healthy children (1 to 2 years of age) vaccinated with two doses of tetravalent meningococcal conjugate vaccine formulated at 4 µg per dose by polysaccharide

| Immune Response By Serogroup | $N_1/N_2/N_3$ | IgG GMC (µg/ml) [95% CI] | | | SBA GMT [95% CI] | | |
|---|---|---|---|---|---|---|---|
| | | Pre dose 1 | Pre dose 2 | Post dose 2 | Pre dose 1 | Pre dose 2 | Post dose 2 |
| A | 8/8/8 | 0.2 [0.1-0.4] | 2.1 [0.9-4.8] | 4.4 [2.1-9.1] | 8.7 [1.4-55.1] | 1328 [179-9871] | 3158 [1857-5371] |
| C | 8/8/8 | 0.2 [0.0-0.7] | 1.0 [0.3-3.1] | 1.5 [0.6-3.6] | 6.7 [2.0-23.0] | 117 [37.7-365] | 304 [128-721] |
| W-135 | 8/8/8 | 0.1 [0.1-0.2] | 0.6 [0.2-1.9] | 1.5 [0.8-3.1] | 6.2 [2.2-17.2] | 22.6 [2.8-185] | 430 [172-1076] |
| Y | 8/8/8 | 0.3 [0.2-0.4] | 1.2 [0.5-2.8] | 4.5 [2.7-7.6] | 5.7 [3.7-8.8] | 98.7 [20.4-478] | 304 [101-920] | vaccine received a booster dose of AC polysaccharide. The reason for the booster dose of polysaccharide was to evaluate whether or not the subjects would elicit an anemestic response.

The results of this study, both the primary and polysaccharide booster immune responses are presented in Table 4 for the IgG antibody response and Table 5 for the SBA antibody response. The IgG antibody response post primary series was approximately the same for both the polysaccharide and conjugate vaccine. However, the bactericidal antibody response in the conjugate vaccinated subjects was much higher than that for the polysaccharide vaccinated subjects. As observed with the one year old subjects, vaccination of infants with the polysaccharide elicits very little functional-bactericidal antibody. The antibody elicited by the infants to the polysaccharide vaccine is presumably low avidity antibody, whereas, the conjugate vaccine appears to elicit high avidity antibody, thereby accounting for the much higher titer of bactericidal antibody. The high level of functional antibody elicited by the booster dose of polysaccharide vaccine in the subjects who had received the conjugate vaccine in the primary vaccination series, indicates that these subjects have been primed for a memory or T-cell dependent antibody response. The subjects who received the polysaccharide vaccine in the primary vaccination series elicited a modest response to the polysaccharide booster dose, that is indicative of a T-cell independent

TABLE 4

Anti-polysaccharide IgG GMC (group mean concentration) in infants against serogroups A and C before and after both the primary series immunization (6, 10 and 14 weeks of age) and the booster vaccination with bivalent AC polysaccharide given at 11 to 12 months of age.

| Immune Response by Vaccine Group | Primary Vaccination GMC [95% CI] | | | PS Booster Vaccination GMC [95% CI] | | |
|---|---|---|---|---|---|---|
| | N | Pre | Post | N | Pre | Post |
| Serogroup A: | | | | | | |
| AC Conjugate | 34 | 3.4 [2.2-5.4] | 5.8 [4.3-8.0] | 31 | 0.2 [0.1-0.3] | 7.0 [4.0-12.0] |
| AC Polysaccharide | 35 | 3.0 [1.7-5.3] | 5.5 [4.1-7.3] | 30 | 0.9 [0.5-1.4] | 3.1 [2.0-4.7] |
| HIB Conjugate | 36 | 3.2 [2.2-4.5] | 0.6 [0.4-0.8] | NA | NA | NA |
| Serogroup C: | | | | | | |
| AC Conjugate | 31 | 1.6 [0.9-2.8] | 2.8 [2.0-3.9] | 31 | 0.1 [0.1-0.2] | 8.1 [4.5-14.5] |
| AC Polysaccharide | 35 | 2.3 [1.4-3.9] | 5.3 [3.8-7.4] | 30 | 0.6 [0.3-1.0] | 2.8 [1.7-4.7] |
| HIB Conjugate | 36 | 2.0 [1.2-3.5] | 0.5 [0.3-0.7] | NA | NA | NA |

TABLE 5

SBA antibody GMT (group mean titer) in infants against serogroups A and C before and after both the primary series immunization (6, 10 and 14 weeks of age) and booster vaccination with bivalent AC polysaccharide given at 11 to 12 months of age.

| Immune Response By Vaccine Group | Primary Vaccination GMT [95% CI] | | | PS Booster Vaccination GMT [95% CI] | | |
|---|---|---|---|---|---|---|
| | N | Pre | Post | N | Pre | Post |
| Serogroup A: | | | | | | |
| AC Conjugate | 34 | 11.8 [7.2-19.3] | 177 [101-312] | 24 | 10.1 [5.6-18.0] | 373 [162-853] |
| AC Polysaccharide | 32 | 14.7 [8.5-25.4] | 7.0 [4.7-10.5] | 26 | 6.1 [3.9-9.5] | 24.1 [11-53] |
| HIB Conjugate | 35 | 11.2 [6.8-18.3] | 6.7 [4.3-10.5] | NA | NA | NA |
| Serogroup C: | | | | | | |
| AC Conjugate | 34 | 50.8 [24-107] | 189 [128-278] | 27 | 4.6 [3.6-5.6] | 287 [96.2-858] |
| AC Polysaccharide | 32 | 62.7 [29-131] | 25.4 [14.4-44.6] | 26 | 4.1 [3.9-4.3] | 14.4 [7.9-26.1] |
| HIB Conjugate | 36 | 45.3 [21.9-133] | 7.3 [4.7-11.3] | NA | NA | NA |

In addition to the benefits that this invention offers to the improved protection against meningococcal disease in young populations and the wider protection against serogroups A, C, W-135 and Y, the tetravalent conjugate may provide protection to other pathogens by inducing an antibody response to the carrier protein. When the tetravalent conjugate vaccine, using diphtheria toxoid conjugate, was administered to infants, these subjects also received the routine pediatric immunizations, which included diphtheria toxoid. Therefore, in these subjects there was no apparent improvement in the antibody response to diphtheria toxoid. However, when the diphtheria toxoid conjugate was administered to subjects that did not receive concomitant diphtheria toxoid containing vaccines, a strong booster response to diphtheria toxoid was observed. These subjects had received a three dose regiment of DTP at 2, 3, and 4 months of age. In this study, the subjects received either single dose of a bivalent AC conjugate or a single dose of bivalent AC polysaccharide vaccine between 2 and 3 year of age. Blood specimens were taken at the time of vaccination and 30-days post vaccination. The bivalent AC conjugate used diphtheria toxoid as the carrier protein.

The immune response of diphtheria toxoid in the two vaccine groups is presented in Table 6. The polysaccharide did not serve to stimulate an anti-diphtheria immune response in these subjects as expected, however a strong anti-diphtheria immune response was observed for the subjects receiving the AC conjugate. Therefore, the meningococcal conjugate vaccine may provide an added benefit of stimulating an immune response to carrier protein thereby providing protection against diseases caused by *Corynebacteria diphtheriae* when diphtheria toxoid is used as a carrier protein.

TABLE 6

Anti-diphtheria antibody by ELISA GMT (group mean titer) in IU/ml in young healthy children vaccinated with either a bivalent AC diphtheria toxoid conjugate vaccine formulated at 4 μg as polysaccharide per dose or a bivalent AC polysaccharide vaccine formulated at 50 μg as polysaccharide per dose

| Immune Response | | Anti-Diphtheria Antibody (ELISA - IU/ml) [95% CI] | |
|---|---|---|---|
| by Vaccine Group | $N_{pre}/N_{post}$ | Pre | Post |
| AC Conjugate | 104/103 | 0.047 [0.036-0.060] | 21.2 [11.6-38.6] |
| AC Polysaccharide | 103/102 | 0.059 [0.045-0.076] | 0.059 [0.045-0.077] |

References:

Frasch, C. E., Zollenger, W. D. and Poolman, J. T. (1985) Review of Infectious Diseases 7, pp. 504-510.

Reido, F. X., Plikaytis, B. D. and Broome, C. V. (1995) Pediatric Infectious Disease Journal 14, pp. 643-657.

Artenstein, M. S., Gold, R., Zimmerly, J. G., Wyle, F. A., Schneider, H. and Harkins, C. (1970) The New England Journal of Medicine 282, pp. 417-420.

Peltola, H., Mäkelä, H., Käyhty, H., Jousimies, H., Herva, E., Hällström, K., Sivonen, A., Renkonen, O. V., Pettay, O., Karanko, V., Ahvonen, P., and Sama, S. (1997) The New England Journal of Medicine 297, pp. 686-691.

Reingold, A. L., Broome, C. V., Hightower, A. W., Ajello, G. W., Bolan, G. A., Adamsbaum, C., Jones, E. E., Phillips, C., Tiendrebeogo, H., and Yada, A. (1985) The Lancet 2, pp. 114-118.

Goldschneider, I., Lepow, M. L., Gotschlich, E. C., Mauck, F. T., Bachl, F., and Randolph, M. (1973) The Journal of Infectious Diseases 128, pp. 769-776.

Gold, R., Lepow, M. L., Goldschneider, I., and Gotschlich, E. C. (1977) The Journal of Infectious Diseases 136, S31-835.

Brandt, B. L. and Artenstein, M. S. (1975) The Journal of Infectious Diseases 131, pp. S69-S72.

Käyhty, H., Karanko, V., Peltola, H., Sarna, S, and Mäkelä, H. (1980) The Journal of Infectious Diseases 142, pp. 861-868.

Cessey, S. J., Allen, S. J., Menon, A., Todd, J. E., Cham, K., Carlone, G. M., Turner, S. H., Gheesling, L. L., DeWitt, W., Plikaytis, B. D., and Greenwood, B. (1993) The Journal of Infectious Diseases 167, pp 1212-1216.

Wyle, F. A., Artenstein, M. S., Brandt, G. L., Tramont, E. C., Kasper, D. L., Altieri, P. L., Berman, S. L., and Lowenthal, J. P. (1972) The Journal of Infectious Diseases, 126, pp. 514-522.

Jennings, H. J. and Lugowski, C. (1981) The Journal of Immunology 127, pp. 1011-1018.

What is claimed is:

1. An immunological composition comprising a mixture of four distinct and separately made protein-capsular polysaccharide conjugates, wherein the first conjugate comprises purified *Neisseria meningitidis* capsular polysaccharide of serogroup W-135 conjugated to a carrier protein, the second conjugate comprises purified *N. meningitidis* capsular polysaccharide of serogroup Y conjugated to a carrier protein, the third conjugate comprises purified *N. meningitidis* capsular polysaccharide of serogroup A conjugated to a carrier protein, and the fourth conjugate comprises purified *N. meningitidis* capsular polysaccharide of serogroup C conjugated to a carrier protein, wherein each of the *N. meningitidis* serogroups A, C, W-135 and Y capsular polysaccharides is derivatized with adipic acid dihydrazide, and wherein the immunological composition elicits, in children less than two years of age, a primary serum IgG response and a serum bactericidal antibody response to each of *N. meningitides* serogroups A, C, W-135 and Y capsular polysaccharides, wherein said serum bactericidal antibody response is higher than that elicited by the licensed, unconjugated, tetravalent A, C, W-135 and Y meningococcal capsular polysaccharide vaccine, and further wherein the immunological composition is capable of eliciting a booster anamnestic IgG response to each of the *N. meningitidis* serogroups A, C, W-135 and Y capsular polysaccharides.

2. The immunological composition of claim 1, wherein the carrier protein is a single protein species.

3. The immunological composition of claim 2, wherein the single carrier protein species is selected from the group consisting of diphtheria toxoid, $CRM_{197}$, and tetanus toxoid.

4. The immunological composition of claim 3, wherein said carrier protein species is diphtheria toxoid.

5. The immunological composition of claim 3, wherein said carrier protein species is $CRM_{197}$.

6. The immunological composition of claim 1 formulated as a sterile liquid.

7. The immunological composition of claim 1 further comprising a pharmaceutically acceptable preservative.

8. The immunological composition of claim 7 wherein the pharmaceutically acceptable preservative is thimerosal.

9. The immunological composition of claim 1, further comprising an adjuvant.

10. The immunological composition of claim 9, wherein the adjuvant is selected from the group consisting of aluminum adjuvants.

11. The immunological composition of claim 10, wherein the adjuvant is aluminum hydroxide.

12. The immunological composition of claim 10, wherein the adjuvant is aluminum phosphate.

13. The immunological composition of one of claims 1-8, wherein the composition is unadjuvanted.

14. A tetravalent conjugate vaccine comprising a mixture of four distinct and separately made protein-capsular polysaccharide conjugates, wherein the first conjugate comprises purified *Neisseria meningitidis* capsular polysaccharide of serogroup W-135 conjugated to a carrier protein, the second conjugate comprises purified *N. meningitidis* capsular polysaccharide of serogroup Y conjugated to a carrier protein, the third conjugate comprises purified *N. meningitidis* capsular polysaccharide of serogroup A conjugated to a carrier protein, and the fourth conjugate comprises purified *N. meningitidis* capsular polysaccharide of serogroup C conjugated to a carrier protein, wherein each of the *N. meningitidis* serogroups A, C, W-135 and Y capsular polysaccharides is derivatized with adipic acid dihydrazide, and wherein the tetravalent conjugate vaccine elicits, in children less than two years of age, a primary serum IgG response and a serum bactericidal antibody response to each of *N. meningitides* serogroups A, C, W-135 and Y capsular polysaccharides, wherein said serum bactericidal antibody response is higher than that elicited by the licensed, unconjugated, tetravalent A, C, W-135 and Y meningococcal capsular polysaccharide vaccine, and further wherein the tetravalent conjugate vaccine is capable of eliciting a booster anamnestic IgG response to each of the *N. meningitidis* serogroups A, C, W-135 and Y capsular polysaccharides.

15. The conjugate vaccine of claim 14, wherein the carrier protein is a single protein species.

16. The conjugate vaccine of claim 14, wherein the single carrier protein species is selected from the group consisting of diphtheria toxoid, $CRM_{197}$, and tetanus toxoid.

17. The conjugate vaccine composition of claim 16, wherein said carrier protein species is diphtheria toxoid.

18. The conjugate vaccine of claim 16, wherein said carrier protein species is $CRM_{197}$.

19. The conjugate vaccine of claim 14, formulated as a sterile liquid.

20. The conjugate vaccine of claim 14, further comprising a pharmaceutically acceptable preservative.

21. The conjugate vaccine of claim 20, wherein the pharmaceutically acceptable preservative is thimerosal.

22. The conjugate vaccine of claim 14, further comprising an adjuvant.

23. The conjugate vaccine of claim 22, wherein the adjuvant is selected from the group consisting of aluminum adjuvants.

24. The conjugate vaccine of claim 23, wherein the adjuvant is aluminum hydroxide.

25. The conjugate vaccine of claim 23, wherein the adjuvant is aluminum phosphate.

26. The conjugate vaccine of one of claims 14-21, wherein the composition is unadjuvanted.

27. The conjugate vaccine of claim 16, wherein said carrier protein species is tetanus toxoid.

28. The immunological composition of claim 3, wherein said carrier protein species is tetanus toxoid.

29. The immunological composition of claim 1, wherein the capsular polysaccharide of each of the serogroups is depolymerized.

30. The tetravalent conjugate vaccine of claim 14, wherein the capsular polysaccharide of each of the serogroups is depolymerized.

31. A method of immunizing children less than two years of age comprising administering to said children an immunological composition comprising a mixture of four distinct and separately made protein-capsular polysaccharide conjugates, wherein the first conjugate comprises purified *Neisseria meningitidis* capsular polysaccharide of serogroup W-135 conjugated to a carrier protein, the second conjugate comprises purified *N. meningitides* capsular polysaccharide of serogroup Y conjugated to a carrier protein, the third conjugate comprises purified *N. meningitidis* capsular polysaccharide of serogroup A conjugated to a purified carrier protein, and the fourth conjugate comprises purified *N. meningitidis* capsular polysaccharide of serogroup C conjugated to a carrier protein, wherein each of the *N. meningitidis* serogroups A, C, W-135 and Y capsular polysaccharides is derivatized with adipic acid dihydrazide, and wherein the administration of the immunological composition elicits in said children a primary serum IgG response and a serum bactericidal antibody response to each of the *N. meningitidis* serogroups A, C, W-135 and Y capsular polysaccharides, wherein said serum bactericidal antibody response is higher than that elicited by the licensed, unconjugated, tetravalent A, C, W-135 and Y meningococcal capsular polysaccharide vaccine, and further wherein the administration of the immunological composition is capable of eliciting a booster anamnestic IgG response to each of the *N. meningitidis* serogroups A, C, W-135 and Y capsular polysaccharides.

32. The method of claim 31, wherein the immunological composition further comprises an adjuvant.

33. The method of claim 32, wherein the adjuvant is an aluminum adjuvant.

34. The method of claim 33, wherein the adjuvant is aluminum phosphate.

35. The method of claim 33, wherein the adjuvant is aluminum hydroxide.

36. The method of claim 31, wherein said carrier protein is a single carrier protein species.

37. The method of claim 36, wherein said single carrier protein species is selected from the group consisting of diphtheria toxoid, $CRM_{197}$ and tetanus toxoid.

38. The method of claim 37, wherein said carrier protein species is diphtheria toxoid.

39. The method of claim 37, wherein said carrier protein species is $CRM_{197}$.

40. The method of claim 37, wherein said carrier protein species is tetanus toxoid.

41. The method of claim 31, wherein the immunological composition is formulated as a sterile liquid.

42. The method of claim 31, wherein the immunological composition further comprises a pharmaceutically acceptable preservative.

43. The method of claim 42, wherein said pharmaceutically acceptable preservative is thimerosal.

44. The method of claim 31, wherein the method includes the administration of a primary dose and a booster dose of the immunological composition.

45. The method of claim 31, wherein the immunological composition is formulated at 4 microgram of each of the *N. meningitidis* serogroups A, C, W-135 and Y capsular polysaccharides per dose of the composition.

46. The method of claim 31, wherein the immunological composition is unadjuvanted.

47. The method of claim 31, wherein the capsular polysaccharide of each of the serogroups is depolymerized.

48. A method of vaccinating children less than two years of age comprising administering to said children a tetravalent conjugate vaccine comprising a mixture of four distinct and separately made protein-capsular polysaccharide conjugates, wherein the first conjugate comprises purified *Neisseria meningitidis* capsular polysaccharide of serogroup W-135 conjugated to a carrier protein, the second conjugate comprises purified *N. meningitides* capsular polysaccharide of serogroup Y conjugated to a carrier protein, the third conjugate comprises purified *N. meningitidis* capsular polysaccharide of serogroup A conjugated to a purified carrier protein, and the fourth conjugate comprises purified *N. meningitidis* capsular polysaccharide of serogroup C conjugated to a carrier protein, wherein each of the *N. meningitidis* serogroups A, C, W-135 and Y capsular polysaccharides is derivatized with adipic acid dihydrazide, and wherein the administration of the tetravalent conjugate vaccine elicits in said children a primary serum IgG response and a serum bactericidal antibody response to each of the *N. meningitidis* serogroups A, C, W-135 and Y capsular polysaccharides, wherein said serum bactericidal antibody response is higher than that elicited by the licensed, unconjugated, tetravalent A, C, W-135 and Y meningococcal capsular polysaccharide vaccine, and further wherein the administration of the tetravalent conjugate vaccine is capable of eliciting a booster anamnestic IgG response to each of the *N. meningitidis serogroups* A, C, W-135 and Y capsular polysaccharides.

49. The method of claim 48, wherein the vaccine further comprises an adjuvant.

50. The method of claim 48, wherein the adjuvant is an aluminum adjuvant.

51. The method of claim 50, wherein the adjuvant is aluminum hydroxide.

52. The method of claim 50, wherein the adjuvant is aluminum phosphate.

53. The method of claim 48, wherein said carrier protein is a single carrier protein species.

54. The method of claim 48, wherein said single carrier protein species is selected from the group consisting of diphtheria toxoid, $CRM_{197}$ and tetanus toxoid.

55. The method of claim 54, wherein said carrier protein species is diphtheria toxoid.

56. The method of claim 54, wherein said carrier protein species is $CRM_{197}$.

57. The method of claim 54, wherein said carrier protein species is tetanus toxoid.

58. The method of claim 48, wherein the vaccine is formulated as a sterile liquid.

59. The method of claim 48, wherein the vaccine further comprises a pharmaceutically acceptable preservative.

60. The method of claim 59, wherein said pharmaceutically acceptable preservative is thimerosal.

61. The method of claim 48, wherein the method includes the administration of a primary dose and a booster dose of the vaccine.

62. The method of claim 48, wherein the vaccine is formulated at 4 microgram of each of the *N. meningitidis* serogroups A, C, W-135 and Y capsular polysaccharides per dose of the vaccine.

63. The method of claim 48, wherein the vaccine is unadjuvanted.

64. The method of claim 48, wherein the capsular polysaccharide of each of the serogroups is depolymerized.

* * * * *

UNITED STATES PATENT AND TRADEMARK OFFICE
CERTIFICATE OF CORRECTION

| | |
|---|---|
| PATENT NO. | : 8,734,813 B2 |
| APPLICATION NO. | : 13/843037 |
| DATED | : May 27, 2014 |
| INVENTOR(S) | : Robert P. Ryall |

Page 1 of 1

It is certified that error appears in the above-identified patent and that said Letters Patent is hereby corrected as shown below:

In the Specification

Column 8, line 20, "and incubated at to" should read --and incubated at 25 to--

Column 8, line 50, "50 C" should read --5° C.--

Signed and Sealed this
Seventh Day of April, 2015

Michelle K. Lee
*Director of the United States Patent and Trademark Office*